US008236560B2

(12) United States Patent
Chaplin et al.

(10) Patent No.: US 8,236,560 B2
(45) Date of Patent: *Aug. 7, 2012

(54) MODIFIED VACCINIA ANKARA VIRUS VARIANT AND CULTIVATION METHOD

(75) Inventors: Paul Chaplin, Munich (DE); Paul Howley, Berwick (AU); Christine Meisinger-Henschel, Neuried (DE); Ingmar Rathe, Olching (DE); Eva Felder, Munich (DE); Karl Heller, Unterfohring (DE)

(73) Assignee: Bavarian Nordic A/S, Kvistgaard (DK)

( * ) Notice: Subject to any disclaimer, the term of this patent is extended or adjusted under 35 U.S.C. 154(b) by 18 days.

This patent is subject to a terminal disclaimer.

(21) Appl. No.: 13/106,176

(22) Filed: May 12, 2011

(65) Prior Publication Data

US 2011/0217757 A1     Sep. 8, 2011

Related U.S. Application Data

(63) Continuation of application No. 12/200,295, filed on Aug. 28, 2008, now Pat. No. 7,964,396, which is a continuation of application No. 11/071,741, filed on Mar. 3, 2005, now Pat. No. 7,445,924, which is a continuation-in-part of application No. 11/071,814, filed on Mar. 3, 2005, now Pat. No. 7,695,939, which is a continuation of application No. PCT/EP03/09704, filed on Sep. 1, 2003, said application No. 11/071,741 is a continuation-in-part of application No. 10/440,073, filed on May 16, 2003, now Pat. No. 7,189,536, which is a continuation of application No. PCT/EP01/13628, filed on Nov. 22, 2001.

(30) Foreign Application Priority Data

Nov. 23, 2000   (DK) ................................ 2000 01764
Sep. 5, 2002    (DK) ................................ 2002 01302

(51) Int. Cl.
    *A01N 63/00*    (2006.01)

(52) U.S. Cl. .................... 435/349; 424/93.7; 424/184.1; 424/232.1; 435/41; 435/235.1; 435/239; 435/325; 435/384

(58) Field of Classification Search .................... None
See application file for complete search history.

(56) References Cited

U.S. PATENT DOCUMENTS

| | | | |
|---|---|---|---|
| 3,887,430 A | 6/1975 | Torney et al. | |
| 4,072,565 A | 2/1978 | Weiss et al. | |
| 5,024,947 A | 6/1991 | Inlow et al. | |
| 5,155,020 A | 10/1992 | Paoletti | |
| 5,185,146 A | 2/1993 | Altenburger et al. | |
| 5,403,582 A | 4/1995 | Nazerian et al. | |
| 5,405,772 A | 4/1995 | Ponting | |
| 5,494,807 A | 2/1996 | Paoletti et al. | |
| 5,550,051 A | 8/1996 | Mundt et al. | |
| 5,753,489 A | 5/1998 | Kistner et al. | |
| 5,756,341 A | 5/1998 | Kistner et al. | |
| 5,789,245 A | 8/1998 | Dubensky et al. | |
| 6,100,061 A | 8/2000 | Reiter et al. | |
| 6,146,873 A | 11/2000 | Kistner et al. | |
| 6,761,893 B2 | 7/2004 | Chaplin et al. | |
| 6,913,752 B2 | 7/2005 | Chaplin et al. | |
| 6,924,137 B2 | 8/2005 | Howley et al. | |
| 7,056,723 B2 | 6/2006 | Heller et al. | |
| 7,097,842 B2 | 8/2006 | Suter et al. | |
| 7,189,536 B2 | 3/2007 | Chaplin et al. | |
| 7,335,364 B2 | 2/2008 | Chaplin et al. | |
| 7,384,644 B2 | 6/2008 | Chaplin et al. | |
| 7,445,924 B2 | 11/2008 | Chaplin et al. | |
| 7,695,939 B2 | 4/2010 | Rathe et al. | |
| 7,964,395 B2* | 6/2011 | Chaplin et al. ................ | 435/349 |
| 7,964,396 B2* | 6/2011 | Chaplin et al. ................ | 435/349 |
| 7,964,397 B2* | 6/2011 | Rathe et al. ................... | 435/349 |
| 7,964,398 B2* | 6/2011 | Chaplin et al. ................ | 435/349 |
| 2002/0022268 A1 | 2/2002 | Xu et al. | |
| 2003/0013190 A1 | 1/2003 | Mayr | |

(Continued)

FOREIGN PATENT DOCUMENTS

EP              0584788 A2       3/1994
(Continued)

OTHER PUBLICATIONS

Hutchings et al., Growth and maintenance of HeLa cells in serum-free medium supplemented with hormones, Proc. Natl. Acad. Sci, USA vol. 75, No. 2, pp. 901-904, Feb. 1978.
Orly et al., Fibronectin Mediates Cytokinesis and Growth of Rat Follicular Cells in Serum-Free Medium, Cell, vol. 17, 295-305, Jun. 1979.
Wille et al., Integrated Control of Growth and Differentiation of Normal Human Prokeratinocytes Cultured in Serum-Free Medium: Clonal Analyses, Growth Kinetics, and Cell Cycle Studies, Journal of Cellular Physiology 121, 31-44 (1984).
Gospodarowicz et al., Growth Factors in Mammalian Cell Culture, Annu. Rev. Biochem. 45, 531-558 (1976).
McMurtry et al., Developmental Changes in Embryonic and Extra-Embryonic Insulin-Like Growth Factor-I Tissue Concentrations in the Turkey Embryo, Poultry Science 76, 894-900 (1997).

(Continued)

*Primary Examiner* — Benjamin P Blumel
(74) *Attorney, Agent, or Firm* — Law Office of Salvatore Arrigo and Scott Lee, LLP

(57) ABSTRACT

The present invention provides an attenuated virus, which is derived from Modified Vaccinia Ankara virus and characterized by the loss of its capability to reproductively replicate in human cell lines. It further describes recombinant viruses derived from this virus and the use of the virus, or its recombinants, as a medicament or vaccine. A method is provided for inducing an immune response in individuals who may be immune-compromised, receiving antiviral therapy, or have a pre-existing immunity to the vaccine virus. In addition, a method is provided for the administration of a therapeutically effective amount of the virus, or its recombinants, in a vaccinia virus prime/vaccinia virus boost inoculation regimen. The present invention relates to a method of virus amplification in primary cells which are cultivated in a serum free medium. Viruses produced by this method are advantageously free of any infectious agents comprised in animal sera.

20 Claims, No Drawings

U.S. PATENT DOCUMENTS

| | | | |
|---|---|---|---|
| 2003/0228330 A1 | 12/2003 | Falkner et al. |
| 2004/0058441 A1 | 3/2004 | Pain et al. |
| 2004/0234950 A1 | 11/2004 | Howley et al. |
| 2005/0214323 A1 | 9/2005 | Chaplin et al. |
| 2005/0214324 A1 | 9/2005 | Rathe et al. |
| 2006/0093620 A1 | 5/2006 | Falkner et al. |
| 2006/0127984 A1 | 6/2006 | Ackermann et al. |
| 2006/0280758 A1 | 12/2006 | Chaplin et al. |
| 2008/0089907 A1 | 4/2008 | Chaplin et al. |
| 2008/0317778 A1 | 12/2008 | Chaplin et al. |
| 2009/0017536 A1 | 1/2009 | Chaplin et al. |
| 2009/0029459 A1 | 1/2009 | Rathe et al. |
| 2010/0111999 A1 | 5/2010 | Guehenneux et al. |
| 2010/0279386 A1 | 11/2010 | Chaplin et al. |

FOREIGN PATENT DOCUMENTS

| | | | |
|---|---|---|---|
| JP | H9-154571 A1 | 6/1997 |
| WO | 92/05246 A1 | 4/1992 |
| WO | 95/22978 A1 | 8/1995 |
| WO | 96/15231 A1 | 5/1996 |
| WO | 97/02355 A1 | 1/1997 |
| WO | 97/02355 A1 | 2/1997 |
| WO | 97/31119 A1 | 8/1997 |
| WO | 98/04680 A1 | 2/1998 |
| WO | 98/15614 A1 | 4/1998 |
| WO | 98/56919 A1 | 12/1998 |
| WO | 99/07869 A1 | 2/1999 |
| WO | 00/28016 A1 | 5/2000 |
| WO | 00/29428 A1 | 5/2000 |
| WO | 01/68820 A1 | 9/2001 |
| WO | 01/89559 A1 | 11/2001 |
| WO | 02/24224 A1 | 3/2002 |
| WO | 02/24876 A2 | 3/2002 |
| WO | 02/42480 A1 | 5/2002 |
| WO | 03/008533 A2 | 1/2003 |
| WO | 03/054174 A1 | 7/2003 |
| WO | 03/054175 A1 | 7/2003 |

OTHER PUBLICATIONS

Karcher et al., Developmental changes in amniotic and allantoic fluid insulin-like growth factor (IGF)-I and -II concentrations of avian embryos, Comparative Biochemistry and Physiology, Part A 142, 404-409 (2005).

Flamme et al., Mitogenic activity of chicken chorioallantoic fluid is temporally correlated to vascular growth in the chorioallantoic membrane and related to fibroblastgrowth factors, Development 111, 683-690 (1991).

Geistlich et al., CDGF (Chicken Embryo Fibroblast-Derived Growth Factor) is Mitogenically Related to TGF-B and Modulates PDGF, bFGF, and IGF-1 Action on Sparse NIH/3T3 Cells, Exp. Cell Res. 204, 329-335 (1993).

Smith et al., Identification of a novel growth factor with transforming activity secreted by individual chick embryos, Development 109, 905-910 (1990).

Glover et al., Interaction of Phenol Red with Estrogenic and Antiestrogenic Action on Growth of Human Breast Cancer Cells ZR-75-1 and T-47-D, Cancer Res. 48, 3693-3697 (1988).

Invitrogen, Technical Resources—Media Formulation of RPMI Medium 1640, Dec. 13, 2010.

Invitrogen, Technical Resources—Media Formulation of MEM liquid, Dec. 13, 2010.

Wikipedia, Growth Factors, Dec. 13, 2010.

Sigma-Aldrich, Attachment Factors, Dec. 13, 2010.

Bavarian Nordic, Response to Oppositions, Opposition EP 11434858, Sep. 8, 2009.

Bavarian Nordic, Response to Preliminary Opinion, Opposition EP 11434858, Dec. 22, 2010.

European Patent Office, Summons and Preliminary Opinion, Opposition EP 11434858, May 18, 2010.

Grund, Response to Preliminary Opinion, Opposition EP 11434858, Dec. 22, 2010.

Cabinet Regimbeau, Response to Preliminary Opinion, Opposition EP 11434858, Dec. 22, 2010 (English Translation).

Cabinet Regimbeau, Opposition, Opposition EP 11434858, Jan. 26, 2009 (English Translation).

Grund, Opposition, Opposition EP 11434858, Jan. 23, 2009.

Baxter Aktiengesellschaft, Opposition, Opposition EP 11434858, Jan. 23, 2009.

Oxford Biomedica, Opposition, Opposition EP 11434858, Jan. 23, 2009.

Sanofi Pasteur, Opposition, Opposition EP 11434858, Jan. 23, 2009.

EP Patent No. 1434858, Amended Patent Claims from Oral Proceeding, Opposition to EP Patent No. 1434858, Jan. 27, 2011.

Grob et al., Role of the Individual Interferon Systems and Specific Immunity in Mice in Controlling Systemic Dissemination of Attenuated Pseudorabies Virus Infection, 1999, Journal of Virology, vol. 73, No. 6, pp. 4748-4754.

Carroll, MW, and Moss, B. 1997, Virology 238:198-211.

Meyer, H, et al. Mapping of deletions in the genome of the highly attenuated vaccinia virus MVA and their influence on virulence. J. Gen. Virol. 1991, 72:1031-1038.

Marhoul, Z, et al. Cultivation of Lednice (Yaba1) virus in goose, duck and chick embryo cells. 1976, Acta Virol. 20:499-505. (Abstract).

Ivanov, I, et al. Propagation of avian pox virus vaccine strains in duck embryo cell line—Dec. 99, 2001, Experimental Pathology and Parasitology 4/6, pp. 46-49.

Asher D.M., Bovine Sera Used in the Manufacture of Biologicals: Current Concerns and Policies of the U.S. Food and Drug Administration Regarding the Transmissible Spongiform Encephalopathies, 1999, Developments in Biological Standardization, vol. 99, pp. 41-44.

Kozak et al., Transmissible Spongiform Encephalopathies (TSE): Minimizing the Risk of Transmission of Biological/Biopharmaceutical Products: an Industry Perspective, 1996, Developments in Biological Standardization, vol. 88, pp. 257-264.

Pietrzkowski, et al. "Dextran T-500 improves survival and spreading of chick embryo cells in serum-free medium" Folia Histochemica et Cytobiologica, vol. 26 No. 3, 1988, p. 123-132.

Stittelaar, et al., Vaccine 19: 3700-3709, 2001.

Sutter and Moss, Proc. Natl. Acad. Sci. USA 89:10847-51, 1992.

Schiefiinger, et al., Proc. Natl. Acad. Sci. USA 89:9977-81, 1992.

Merchlinsky, et al., Virology 190:522-6, 1992.

Moss, et al. "Host range restricted, non-replicating vaccinia vires vectors as vaccine candidates." Advances in Experimentaly Medicine and Biology, 397:7-13, 1996.

Wyatt, et al., PNAS 101:4590-4595, 2004.

Earl, et al., Nature 428: 182-185, 2004.

A. Mayr, ZBL Vet B 23, 417-430 (1976).

Blanchard, JT, et al., Journal of General Virology, 79, 1159-1167, 1998.

Bender, et al. Journal of Virology, vol. 70, No. 9, p. 6418-6424, 1996.

Schneider, et al. Nature Medicine, 4, 397-402, 1998.

Sutter, et al. Vaccine 12, 1032-1040, 1994.

Eo, et al., The Journal of Immunology 166: 54735479, 2001.

Holzer, et al., Journal of Virology 73: 4536-4542, 1998.

Antoine, et al., Virology 244: 365-396, 1998.

Gilbert, et al., Biol. Chem. 380: 299-303, 1999.

Behera, et al., Hum. Gene Ther. 13 (14): 1697-709, 2002.

Belyakov, et al., Proc. Natl. Acad. Sci. 100: 9458-9463, 2003.

Hanke, et al., Journal of Viroogy 73: 7524-7532, 1999.

Dollenmeier et al., Proliferation and Differentiation of Chick Skeletal Muscle Cells Cultured in a Chemically Defined Medium, Exp. Cell. Res. 135:47-61 (1981).

Biochrom AG, BMS Serum Alternative, Cat. No. S 5173. Siete 1, von 2.

Balk et al., Epidermal growth factor and insulin cause normal chicken heart mesenchymal cells to proliferate like their Rous sarcoma virus-infected counterparts, Proc. Nat. Acad. Sci. USA 79: 1154-1157 (1982).

Couchman et al.,Fibronectin Has a Dual Role in Locomotion and Anchorage of Primary Chick Fibroblasts and Can Promote Entry into the Division Cycle, J. Cell. Biol. 93: 402-410 (1982).

Kwon et al., Test on Growth and Maintenance Examination of Chick Embryo Fibroblast in the Medium to Which Chicken Embryo Amnio-Allantoic Fluid is Added Instead of Bovine Serum, Agriculture Test Research Report No. 20 (Livestock Hygiene Sericulture Section): 5-9 (1978).

Nakamura et al., Tyrosine Phosphorylation of Specific Proteins After Mitogen Stimulation of Chicken Embryo Fibroblasts, Mol. Cell Biol. 3:380-390 (1983).

Pietrzkowski et al., Cellular Activities Associated with the Transition of Chick Embryo Fibroblasts from Stationary to Proliferation State, Folia Histochemica et Cytobiologica vol. 27:183-196 (1969).

Price et al., Serum-Free Medium Without Animal Components for Virus Production, FOCUS vol. 19 No. 3, 67-69 (1997).

Zell-Und Gewebekultur, Einführung in die Grundlagen sowie ausgewählte Methoden und Anwendungen, Lindl et al., Gustav Fischer Verlag, Stuttgart, New York, p. 57 (1987).

Life Technologies, Product description of VP-SFM (May 1999).

Focus on Alternatives, Serum Free Media for Cell Culture (Aug. 2006).

Geistlich and Gehring, Isolation and characterization of a novel type of growth factor derived from serum-free conditioned medium of chicken embryo fibroblasts, European Journal of Biochemistry 207: 147-153, 1992.

* cited by examiner

MODIFIED VACCINIA ANKARA VIRUS VARIANT AND CULTIVATION METHOD

This application is a continuation of U.S. application Ser. No. 12/200,295, filed Aug. 28, 2008, which is a continuation of U.S. application Ser. No. 11/071,741, filed Mar. 3, 2005, now U.S. Pat. No. 7,445,924, which is a continuation-in-part of U.S. Application Ser. No. 11/071,814, filed Mar. 3, 2005, now U.S. Pat. No. 7,695,939, which is a continuation of International Application PCT/EP03/009704, filed Sep. 1, 2003, which claims the benefit of PA 2002 01302, filed Sep. 5, 2002, in Denmark. U.S. application Ser. No. 11/071,741 is also a continuation-in-part of U.S. application Ser. No. 10/440,073, filed May 16, 2003, now U.S. Pat. No. 7,189,536, which is a continuation of International Application PCT/EP01/13628, filed Nov. 22, 2001, which claims the benefit of PA 2000 01764, filed Nov. 23, 2000, in Denmark. All of these applications are incorporated by reference herein.

FIELD OF THE INVENTION

The present invention provides an attenuated virus which is derived from Modified Vaccinia Ankara virus and which is characterized by the loss of its capability to reproductively replicate in human cell lines. It further describes recombinant viruses derived from this virus and the use of the virus or its recombinants as a medicament or vaccine. Additionally, a method is provided for inducing an immune response even in immune-compromised patients, patients with pre-existing immunity to the vaccine virus, or patients undergoing antiviral therapy. The present invention also provides a method for the cultivation of primary cells. The primary cells are cultivated in a serum free medium comprising a factor selected from the group consisting of growth factors and attachment factors. The method for the cultivation of primary cells may be one step in a method for the amplification of viruses, wherein the cells are then infected with a subject virus and the infected cells are cultivated in serum free medium until progeny virus is produced. The invention encompasses the cultivation of poxviruses according to this method.

BACKGROUND OF THE INVENTION

Modified Vaccinia Ankara (MVA) virus is related to vaccinia virus, a member of the genera *Orthopoxvirus* in the family of Poxyiridae. MVA was generated by 516 serial passages on chicken embryo fibroblasts of the Ankara strain of vaccinia virus (CVA) (for review see Mayr, A., et al. Infection 3, 6-14 [1975]). As a consequence of these long-term passages, about 31 kilobases of the genomic sequence were deleted from the virus and, therefore, the resulting MVA virus was described as being highly host cell restricted to avian cells (Meyer, H. et al., J. Gen. Virol. 72, 1031-1038 [1991]). It was shown in a variety of animal models that the resulting MVA was significantly avirulent (Mayr, A. & Danner, K. [1978] Dev. Biol. Stand. 41: 225-34). Additionally, this MVA strain has been tested in clinical trials as a vaccine to immunize against the human smallpox disease (Mayr et al., Zbl. Bakt. Hyg. I, Abt. Org. B 167, 375-390 [1987], Stickl et al., Dtsch. med. Wschr. 99, 2386-2392 [1974]). These studies involved over 120,000 humans, including high-risk patients, and proved that compared to vaccinia based vaccines, MVA had diminished virulence or infectiousness while it induced a good specific immune response.

In the following decades, MVA was engineered for use as a viral vector for recombinant gene expression or as a recombinant vaccine (Sutter, G. et al. [1994], Vaccine 12: 1032-40).

In this respect, it is significant that even though Mayr et al. demonstrated during the 1970s that MVA is highly attenuated and avirulent in humans and mammals, some recently reported observations (Blanchard et al., 1998, J Gen Virol 79, 1159-1167; Carroll & Moss, 1997, Virology 238, 198-211; Altenberger, U.S. Pat. No. 5,185,146; Ambrosini et al., 1999, J Neurosci Res 55(5), 569) have shown that MVA is not fully attenuated in mammalian and human cell lines since residual replication might occur in these cells. It is assumed that the results reported in these publications have been obtained with various known strains of MVA since the viruses used essentially differ in their properties, particularly in their growth behavior in various cell lines.

Growth behavior is recognized as an indicator for virus attenuation. Generally, a virus strain is regarded as attenuated if it has lost its capacity or only has reduced capacity to reproductively replicate in host cells. The above-mentioned observation, that MVA is not completely replication incompetent in human and mammalian cells, brings into question the absolute safety of known MVA as a human vaccine or a vector for recombinant vaccines.

Particularly for a vaccine, as well as for a recombinant vaccine, the balance between the efficacy and the safety of the vaccine vector virus is extremely important.

Most viral vaccines such as attenuated or recombinant viruses are manufactured from cell culture systems. The cells used for virus/vaccine production may be cell lines, i.e. cells that grow continuously in vitro, either as single-cell suspension culture in bioreactors or as a monolayer on a cell-support surface of tissue culture flasks or roller-bottles. Some examples for cell lines used for the production of viruses are: the human fetal lung cell-line MRC-5 used for the manufacture of polio viruses and the human fetal lung cell-line WI-38 used for the manufacture of measles virus, mumps virus and rubella virus (MMR II) (Merck Sharp & Dohme).

Not only cell lines but also primary animal cells are used for the manufacture of vaccines. An example of primary cells that are used for virus production are chicken embryo fibroblasts (CEF cells). These cells are used for the production of measles and Japanese encephalitis virus (Pasteur Merieux), mumps virus (manufactured by Provaccine), rabies virus (manufactured by Chiron Berhing GmbH & Co.), yellow fever virus (manufacture by Aprilvax), influenza virus (manufactured by Wyeth Labs and SmithKline & Beecham) and modified Vaccinia virus Ankara (MVA).

CEF cells are often used since many virus vaccines are made by attenuating the virulent disease-causing virus by serially passaging in CEF cells. Attenuated viruses, such as MVA are preferably not propagated on human cells since there is a concern that the viruses might become replication competent in cells of human origin. Viruses that have regained the ability to replicate in human cells represent a health risk if administered to humans, in particular if the individuals are immune compromised. For this reason, some attenuated viruses, such as MVA, are strictly manufactured from CEF cells, if intended for human use.

Moreover, CEF cells are used for those viruses that grow only on said cells. Examples of such viruses are avian viruses such as avipox viruses, canary pox virus, ALVAC, Fowl pox virus and NYVAC.

Cell lines and primary cells grown under in vitro culturing conditions require a special growth and maintenance medium that can support (I) cell replication in the logarithmic phase and (II) cell maintenance once the cells are no longer dividing, i.e., when the cells are in the stationary phase. The commonly used cell culture media comprise a rich salt solution containing vitamins, amino acids, essential trace elements and sugars. Growth hormones, enzymes and biologically active proteins required for supporting cell growth and maintenance are usually added as a supplement to the medium in the form of an animal blood derived serum product. Examples of animal blood derived serum products are fetal calf serum, chicken serum, horse serum and porcine serum. These sera are derived from fractionated blood, from which the red blood cells and the white blood cells have been removed. Primary cells, such as CEF cells are even more dependant on animal serum sources than cell lines. Thus, primary cells are usually cultivated in cell culture media comprising 5 to 10% serum, in most cases fetal calf serum (FCS).

The animal sera not only comprise factors that are required for the growth of cells, but also factors that are required for cells that naturally grow as adherent cells to attach to the cell support surface of the culture vessel. Thus, it is critical for adherent cells that enough serum is added to the medium to enable them to grow and form a monolayer.

Unfortunately, bovine/fetal calf serum as well as sera from other animals may contain adventitious pathogenic agents such as viruses or prion proteins. There is a potential risk that these pathogenic agents may be transmitted to the animal/human to be treated or vaccinated with the vaccine or any other pharmaceutical product produced in cell culture. This is of particular relevance if cell culture products are administered to immune-compromised humans. One of the many potential major problems associated with the commonly used bovine serum supplement is the possibility to transmit the agent causing bovine spongiforme encephalopathy (BSE) to the animals/humans that come into contact with the products produced from cell culture.

In view of the possible risk associated with the use of animal sera in cell culture it has become clear that manufacturing processes free from the use of animal products are highly desirable.

To this end, specific media that do not have to be supplemented with animal sera have been developed for continuously growing cell lines and for the production of viruses in continuously growing cell lines, respectively. An example of such a serum free medium that can be used to cultivate cell lines is VP-SFM manufactured by Gibco BRL/Life Technologies. According to the manufacturer's information VP-SFM is designed specifically for the growth of VERO, COS-7, MDCK, Hep2, BHK-21 and other important cell lines (Price, P. and Evege, E. Focus 1997, 19: 67-69) and for virus production in said cell lines. No information is available regarding the cultivation of primary cells in the medium.

THE PRESENT INVENTION

Summary of the Invention

What we therefore believe to be comprised by our invention may be summarized inter alia in the following words:
A method for the amplification of a virus comprising:
cultivating primary avian cells permissive for productive replication of the virus in a serum free medium comprising a factor selected from the group consisting of growth factors and attachment factors,
infecting of the primary avian cells with the virus,
cultivating the infected cells in serum free medium until progeny virus is produced, and
isolating the virus from the culture; such a
method wherein the serum free medium comprising growth factors and attachment factors is removed at the time of infecting the primary avian cells with the virus, and/or during cultivating of the infected cells until virus progeny is produced, and replaced with a serum free medium which does not comprise growth factors and attachment factors; such a method wherein, subsequent to cultivating the infected cells in serum free medium until progeny virus is produced, one or more virus purification steps are performed; such a method wherein the virus used for infection of primary avian cells was previously propagated or may have been previously propagated in the presence of animal sera and is subsequently re-derived through several rounds of plaque purification by limited dilution in serum free medium to reduce the risk of serum contamination; such a method which is repeated at least once to obtain a virus or virus stock which is essentially free of products and/or infectious agents comprised in animal sera; such a method wherein the primary avian cells are Chicken Embryo Fibroblasts (CEF); such a method wherein the growth factor is an epidermal growth factor (EGF); such a method wherein the epidermal growth factor (EGF), is recombinant-human EGF; such a method wherein the concentration of EGF is in a range of 5 to 20 ng/ml medium; such a method wherein the attachment factor is fibronectin; such a method wherein the concentration of fibronectin is in the range of 1 to 10 ug/cm$^2$ surface of the cell culture vessel; such a method wherein the medium comprises two or more factors selected from growth factors and attachment factors; such a method wherein the medium comprises EGF and fibronectin in concentration ranges of 5 to 20 ng/ml and 1 to 10 ug/ml medium, respectively; such a method wherein the medium further comprises one or more additives selected from a microbial extract, a plant extract and an extract from a non-mammalian animal; such a method wherein the microbial extract is a yeast extract or a yeastolate ultrafiltrate; such a method wherein the plant extract is a rice extract or a soya extract; such a method wherein the extract from a non-mammalian animal is a fish extract; such a method wherein the virus is selected from mumps virus, measles virus, rabies virus, Japanese encephalitis virus, yellow fever virus, influenza virus and poxvirus; such a method wherein the poxvirus is an attenuated virus or a recombinant virus; such a method wherein the poxvirus is an orthopoxvirus; such a method wherein the orthopoxvirus is a Vaccinia virus; such a method wherein the Vaccinia virus is Modified Vaccinia virus Ankara; such a method wherein the Modified Vaccinia virus Ankara is selected from MVA-575 deposited at the European Collection of Animal Cell Cultures (ECACC) under the deposition number V00120707, MVA-572 deposited at ECACC under the deposition number V94012707, and MVA-BN deposited at ECACC under number V00083008, or a derivative of any such virus; such a method wherein the Vaccinia virus is an MVA-derived vaccinia virus characterized by replicating in vitro in chicken embryo fibroblasts and by being non-replicative in vitro in human cells which permit replication of MVA vaccinia strain 575 (ECACC V00120707) and/or MVA vaccinia strain 572 (ECACC V94012707); such a method wherein the MVA-derived vaccinia virus is further characterized as being non-replicative in an immunocompromised mouse; such a method of wherein the mouse is an AGR129 transgenic mouse; such a poxvirus obtained by:
cultivating primary avian cells permissive for productive replication of the virus in a serum free medium comprising a factor selected from the group consisting of growth factors and attachment factors,
infecting the primary avian cells with the virus,
cultivating the infected cells in serum free medium until progeny virus is produced, and
isolating the virus from the culture; such a poxvirus wherein the primary avian cells are Chicken Embryo Fibroblasts (CEF); such a poxvirus wherein the virus used for infection of primary avian cells was previously propagated or may have been previously propagated in the presence of animal sera and which virus is subsequently re-derived through several rounds of plaque purification by limited dilution in serum free medium; such a poxvirus wherein 4-6 rounds of plaque purification are performed; such a poxvirus wherein the risk of the poxvirus to contain a BSE particle is less than $10^{32}$; such a poxvirus which is essentially free of any products and/or infectious agents comprised in animal sera; such a poxvirus wherein the poxvirus is Modified Vaccinia virus Ankara; such a poxvirus wherein the Modified Vaccinia virus Ankara is selected from MVA-575 (ECACC V00120707), MVA-572 (ECACC V94012707), and MVA-BN (ECACC V00083008), or a derivative of such virus; such a poxvirus wherein the poxvirus is an MVA-derived vaccinia virus characterized by replicating in vitro in chicken embryo fibroblasts and by being non-replicative in vitro in human cells which permit replication of MVA vaccinia strain 575 (ECACC V00120707) and/or MVA vaccinia strain 572 (ECACC V94012707); such a poxvirus wherein the MVA-derived vaccinia virus is further characterized as being non-replicative in an immunocompromised mouse; such a poxvirus wherein the mouse is an AGR129 transgenic mouse; such a poxvirus wherein the poxvirus is Modified Vaccinia virus Ankara; such a poxvirus wherein the Modified Vaccinia virus Ankara is selected from MVA-575 (ECACC V00120707), MVA-572 (ECACC V94012707), and MVA-BN (ECACC V00083008), or a derivative of such virus; such a poxvirus wherein the poxvirus is an attenuated virus or a recombinant virus; such a vaccine comprising the poxvirus; such a pharmaceutical composition comprising the poxvirus and a pharmaceutically acceptable carrier, diluent and/or additive; such a pharmaceutical composition which is essentially free of any products and/or infectious agents comprised in animal sera; such a method for enhancing a specific immune response to a vaccine in a living mammal, including a human, comprising administering a vaccine and an adjuvant-effective amount of the poxvirus; such a method for affecting a specific immune response in a living mammal, including a human, comprising administering an effective amount of a poxvirus; such a method wherein the specific immune response is against an *orthopox* virus; such a method wherein the specific immune response is against smallpox; such a method for affecting an immune response against an HIV in a living mammal, including a human, comprising administering an effective amount of a poxvirus; such a method for affecting an immune response in a living mammal, including a human, comprising administering an effective amount of a poxvirus; such a method wherein the poxvirus is administered to a cancer patient; such a method wherein the mammal, including a human, is immune compromised; such a method wherein the poxvirus is administered as a vaccine; such a method for inducing a specific immune response in a living mammal, including a human, comprising administering an effective amount of a poxvirus; such a method wherein the specific immune response is against an *orthopox* virus; such a method wherein the specific immune response is against smallpox; such a method wherein the mammal, including a human, is immune compromised; such a method wherein the poxvirus is administered as a vaccine; such a method for inducing an immune response against an HIV in a living mammal, including a human, comprising administering an effective amount of a poxvirus; such a method for inducing an immune response in a living mammal, including a human, comprising administering an effective amount of a poxvirus; such a method wherein the poxvirus is administered to a cancer patient; such a kit for prime/boost immunization comprising the pharmaceutical composition for a first inoculation ("priming inoculation") in a first vial/container and for a second inoculation ("boosting inoculation") in a second vial/container; such a MVA-derived vaccinia virus characterized by replicating in vitro in CEF cells and being non-replicative in vitro in human cells which permit replication of MVA vaccinia virus strain 572 (ECACC V94012707); such a MVA-derived vaccinia virus which is non-replicative in an immunocompromised mouse; such a MVA-derived vaccinia virus, wherein the mouse is an AGR129 transgenic mouse.

DETAILED DESCRIPTION OF THE INVENTION

According to a preferred embodiment of the present invention, new vaccinia viruses are provided which are capable of reproductive replication in non-human cells and cell lines, especially in chicken embryo fibroblasts (CEF), but not capable of reproductive replication in a human cell line known to permit replication with known vaccinia strains.

Known vaccinia strains reproductively replicate in at least some human cell lines, in particular the human keratinocyte cell line HaCaT (Boukamp et al. 1988, J Cell Biol 106(3): 761-71). Replication in the HaCaT cell line is predictive for replication in vivo, in particular for in vivo replication in humans. It is demonstrated in the example section that all known vaccinia strains tested that show a residual reproductive replication in HaCaT also replicate in vivo. Thus, the invention relates to vaccinia viruses that do not reproductively replicate in the human cell line HaCaT. Advantageously, the invention concerns vaccinia virus strains that are not capable of reproductive replication in any of the following human cell lines: human cervix adenocarcinoma cell line HeLa (ATCC No. CCL-2), human embryo kidney cell line 293 (ECACC No. 85120602), human bone osteosarcoma cell line 143B (ECACC No. 91112502) and the HaCaT cell line.

The growth behaviour or amplification/replication of a virus is normally expressed by the ratio of virus produced from an infected cell (Output) to the amount originally used to infect the cell in the first place (Input) ("amplification ratio"). A ratio of "1" between Output and Input defines an amplification status wherein the amount of virus produced from the infected cells is the same as the amount initially used to infect the cells. This ratio is understood to mean that the infected cells are permissive for virus infection and virus reproduction.

An amplification ratio of less than 1, i.e., a decrease of the amplification below input level, indicates a lack of reproductive replication and thus, attenuation of the virus. Therefore, it was of particular interest to identify and isolate a strain that exhibits an amplification ratio of less than 1 in several human cell lines, in particular all of the human cell lines 143B, HeLa, 293, and HaCaT.

Thus, the term "not capable of reproductive replication" means that the virus of the present invention exhibits an amplification ratio of less than 1 in human cell lines, such as 293 (ECACC No. 85120602), 143B (ECACC No. 91112502), HeLa (ATCC No. CCL-2) and HaCaT (Boukamp et al. 1988, J Cell Biol 106(3): 761-71) under the conditions outlined in Example 10 of the present specification. Preferably, the amplification ratio of the virus of the invention is 0.8 or less in each of the above human cell lines, i.e., HeLa, HaCaT, and 143B.

Viruses of the invention are demonstrated not to reproductively replicate in cell lines 143B, HeLa and HaCaT. The particular strain of the invention that has been used in the examples is a derivative of a virus deposited on Aug. 30, 2000 at the European Collection of Cell Cultures (ECACC) under number V00083008. This strain is referred to as "MVA-BN" throughout the Specification. It has already been noted that known MVA strains show residual replication in at least one of the human cell lines tested. All known vaccinia strains show at least some replication in the cell line HaCaT, whereas the MVA strains of the invention, in particular MVA-BN, do not reproductively replicate in HaCaT cells.

Moreover, the invention concerns derivatives of the virus as deposited under ECACC V0083008. "Derivatives" of the viruses as deposited under ECACC V00083008 refer to viruses exhibiting essentially the same replication characteristics as the deposited strain but exhibiting differences in one or more parts of its genome and/or cultured in different media including serum containing and/or serum free media. Viruses having the same "replication characteristics" as the deposited virus are viruses that replicate with similar amplification ratios as the deposited strain in CEF cells and the cell lines HeLa, HaCaT and 143B; and that show a similar replication in vivo, as determined in the AGR129 transgenic mouse model (see below).

Advantageously, the virus of the instant invention is further characterized in that it is cultured under stringent conditions. The present invention provides a method for cultivation of primary cells, in particular primary avian cells, in serum free medium and a method for the production of virus in primary cells under serum free conditions. The instant method for the cultivation of primary cells may be characterized in that the cells are cultivated in a serum free medium comprising a factor selected from the group consisting of growth factors and attachment factors.

According to the present invention primary cells that naturally grow as adherent cells attach to the surface of the cell culture vessel after seeding and grow in a logarithmic phase until a monolayer is formed. According to the present invention the resting cells may be maintained in the medium used during the attachment and logarithmic growth of the cells.

The term "primary cells" as used in the present description is well known to a person skilled in the art. Without being restricted to the following definition the term "primary cells" may refer to cells that have been freshly isolated from an animal or human tissue, organ or organism, wherein the cells are not able to continuously and indefinitely replicate and divide. Usually, primary cells divide in cell culture less than 100 times, often less than 50 times, often less than 25 times. Thus, primary cells have not undergone an immortalizing event. Examples for primary cells are cord blood lymphocytes and human or animal fibroblasts. Representative examples of animal fibroblasts are avian fibroblasts, such as Chicken Embryo Fibroblasts (CEF cells). An example of primary human fibroblasts is human foreskin fibroblasts.

Methods of isolating primary cells are known. Generally, primary cell cultures are derived directly from tissues, organs or embryos. The tissues, organs or embryos are subjected to protease treatment to obtain single cells. The cells are then cultivated according to the method of the present invention under in vitro culture conditions.

More specifically, CEF cells are obtained from protease digested chicken embryos. CEF cells grow best as adherent cells attached to a solid cell support surface. The cells start replication and establish a monolayer. If CEF cells (after embryo digestion) are cultivated in vitro with a standard culturing medium and without animal serum, the cells will occasionally attach to the solid cell-support surface, but will not replicate to form a confluent monolayer of cells and will, with time, slowly detach from the solid culturing-support surface. In contrast, if the CEF cells are cultivated according to the method of the present invention, the cells attach to the solid support, grow in the logarithmic phase until a monolayer is formed and can be maintained in the stationary phase for several days.

The method of the present invention is not restricted to cells that form monolayers. According to an alternative embodiment the method according to the present invention may be used for all other types of primary cells, such as cells naturally growing in suspension culture (e.g. lymphocytes or other types of blood cells) or cells that naturally would grow as adherent cells but have been adapted to growing in suspension culture.

As shown below the cells can also be used for the serum free amplification of viruses that might be useful as vaccines.

Viruses, including e.g. wild-type viruses, attenuated viruses and recombinant viruses that are used as vaccines, may be amplified under serum containing conditions. However as noted above, there is a potential risk that serum contains pathogenic agents (such as TSE/BSE) may be transmitted to the animal/human treated or vaccinated with the vaccine. To reduce the risk of contaminants in the vaccine, it is a further aspect of the invention to passage and/or cultivate and/or plaque purify and/or purify by limited dilution or any other method under serum free conditions those viruses that previously have been amplified under serum containing conditions and that have been used or are intended to be used as vaccine. A virus that may by used in a vaccine and that is passaged and/or cultivated and/or plaque purified and/or purified by limited dilution or any other method under serum free conditions may be a wild-type virus, an attenuated virus or a recombinant virus.

It was unexpected that primary cells naturally growing as adherent cells (I) can effectively attach to the surface of the cell culture vessel without forming unacceptable amounts of aggregates and (II) can be grown in the logarithmic phase in the absence of serum since it is generally believed that primary cells are dependant on a multitude of different factors and components comprised in serum. Moreover, it is believed that adherent cells form non-viable aggregates that do not attach to the surface of the cell culture vessel, when cultivated in serum free medium. Thus, it was unexpected that it is sufficient to add to a serum free medium a factor selected from the group consisting of growth factors and attachment factors in order to obtain attachment and growth of adherent primary cells. Moreover, it was also unexpected that primary cells cultivated in suspension culture can be grown with the media used in the method according to the present invention.

Furthermore, it was surprising that primary avian cells, such as the instant Chicken Embryo Fibroblasts (CEF), can be cultivated to attach to the surface of a cell culture vessel without forming unacceptable amounts of aggregates in a serum free medium comprising a factor selected from the group consisting of growth factors and attachment factors. Avian cells are otherwise understood to grow adversely in serum free medium not comprising growth factors or attachment factors, i.e., it was unexpected that the poor growth properties of primary avian cells could be improved significantly by adding a factor selected from growth factors and attachment factors to serum free medium.

The term "cultivation of cells" in a serum free medium in the context of adherent primary cells refers to the seeding of the cells into the culture vessel in a serum free medium, to the growing of the cells in a serum free medium in the logarithmic phase until a monolayer is formed and/or to the maintenance of the cells in serum free medium as soon as the monolayer is formed. The term "cultivation of cells" in a serum free medium also refers to a method in which all of the above mentioned steps are performed with serum free medium, so that no animal serum products are present during the whole cultivation process of the cells. Thus, in a more general meaning the term "cultivation of cells in a serum free medium" refers to the fact that all media leading to the formation of a monolayer are serum free media. The media used in all of the above steps may comprise a factor selected from growth factors and attachment factors. However, it might be sufficient to add such a factor only to the media used for the attachment of the cells and/or the growing of the cells under logarithmic conditions.

The term "cultivation of cells" in a serum free medium in the context of cells growing in suspension culture refers to the seeding of the cells into the culture vessel in a serum free medium, the growing of the cells in a serum free medium in the logarithmic phase and/or the maintenance of the cells in serum free medium as soon as the saturation density at which no further replication occurs is obtained. The term "cultivation of cells" in a serum free medium refers to a method in which all of the above mentioned steps are performed with serum free medium, so that no animal serum products are present during the whole cultivation of the cells. The media used in all of the above steps may preferably comprise a factor selected from the group of growth factors. However, it might be sufficient to add such a factor only to the media used for the seeding of the cells and/or the growing of the cells under logarithmic conditions. As explained below in more detail it might also be possible to cultivate cells that would normally grow as attached cells also as suspension culture cells if appropriate incubation conditions are chosen (e.g. by applying "wave" incubation). The method according to the present invention also applies for this type of incubation.

The term "serum-free" medium refers to any cell culture medium that does not contain sera from animal or human origin. Suitable cell culture media are known to the person skilled in the art. These media comprise salts, vitamins, buffers, energy sources, amino acids and other substances. An example of a medium suitable for the serum free cultivation of CEF cells is medium 199 (Morgan, Morton and Parker; Proc. Soc. Exp. Biol. Med. 1950, 73, 1; obtainable inter alia from LifeTechnologies).

The media used according to the method of the present invention, in particular the media used for adherent cells such as CEF cells, contain a factor selected from the group consisting of growth factors and attachment factors. An example of an attachment factor is fibronectin.

For cells that naturally grow as adherent cells, which, however, are nevertheless cultivated in suspension culture (which is possible e.g. for CEF cells), it is a further aspect of the invention to use a factor selected from growth factors. Examples of growth factors useful for this type of cultivation are recombinant bovine, mouse, chicken, human epidermal growth factor (EGF), particularly recombinant human EGF (rh-EGF) (Chemicon Int., catalog number: GF001).

For cells naturally growing in suspension culture the medium may comprise a factor selected from the group of growth factors including EGF. Growth factors for these types of cells are factors specific for non-adherent cells. Examples of these growth factors are interleukins, GM-CSF, G-CSF and others. The person skilled in the art may easily determine by routine experimentation, which type of factor is suitable for which type of cells.

If the factor added to the serum free medium is EGF, in particular rh-EGF, it is an aspect of the invention to add such growth factor to the medium at a concentration of 1 to 50 ng/ml. It is a further aspect to add such factor at a concentration of 5 to 20 ng/ml. However, the person skilled in the art will be aware of the fact that different cell types may require a somewhat different concentration of EGF in the medium for optimal results.

If the attachment factor added to the serum free medium is fibronectin: (e.g. Chemicon Int.; Human plasma fibronectin; catalog number FC010), it is an aspect of the invention to add such factor to the medium at a concentration of 1 to 50. It is a further aspect to add such factor at a concentration of 1 to 10 $\mu g/cm^2$ surface of the cell culture vessel. However, those skilled in the art understand that different cell types may require a somewhat different concentration of fibronectin in the medium for optimal results.

It is sufficient to add only one factor selected from growth factors and attachment factors to the medium, in particular if the cells are adherent cells. However, it is also possible to add two or more factors selected from growth factors and attachment factors to the medium. The medium may comprise EGF and fibronectin, possibly in the concentration ranges defined above, in particular if the primary cells are adherent cells such as CEF cells.

The medium may further comprise one or more additives selected from microbial extracts, plant extracts and extracts from non-mammalian animals. The microbial extract may be a yeast extract or yeastolate ultrafiltrate. The plant extract may be a rice extract or soya extract. The extract from non-mammalian animals may be a fish extract.

Asparagine may also be added to the commercially available serum free medium to which a factor selected from growth factors and attachment factors has been added. Asparagine may also be added to the medium that is used during the infection with virus (see below). Commercial serum free media usually comprise asparagine in a concentration range of 0.3 to 1.0 mM. It is an aspect of the invention to add asparagine to supplement the medium in the range of 0.5 to 1.5 mM. A 1 mM asparagine supplement may be adequate. The total concentration of asparagine in the medium is less than 2 mM, in the range of 0.8 to 1.8 mM. For example, the concentration of asparagine in the medium is 1.3 mM.

Moreover, glutamine may also be added to the medium. Glutamine may also be added to the medium that is used during the infection with virus (see below). Glutamine may also be added to supplement the medium at concentrations in the range of 1 to 5 mM. It is a further aspect of the invention to add glutamine at a concentration in the range of 2 to 4 mM. The indicated ranges also correspond to the total concentrations in the medium since most of the commercially available media do not contain glutamine.

Amplification of a virus may comprise the following steps: in the first step primary cells are cultivated according to the method described above, i.e. primary cells are cultivated in a serum free medium comprising a factor selected from the group consisting of growth factors and attachment factors, depending on the cell type. All conditions and definitions given in the description of the method for the cultivation of primary cells above also apply to the definition of the first step of the method for the amplification of virus according to this embodiment of the present invention. In a second step the primary cells are infected with the virus. In the third step the infected cells are incubated in serum free medium until progeny virus is produced. Finally, in a fourth step, the virus is isolated from infected cells.

The term "amplification of a virus" is used to make clear that the method according to the present invention is typically used to increase the amount of virus due to a productive viral replication of the virus in the infected cells. In other words the ratio of output virus to input virus should be above 1. Primary cells are chosen for a specific virus in which the virus is able to productively replicate. The term "reproductive replication" refers to the fact that the specific virus replicates in the specific primary cell to such an extent that infectious progeny virus is produced, wherein the ratio of output virus to input virus is above 1.

The selection of primary cell type which supports productive replication of a particular virus is known. By way of example the primary cells may be human foreskin fibroblasts if the virus to be amplified is the human Cytomegalovirus; the primary cells may be CEF cells if the virus to be amplified is measles virus, mumps virus, rabies virus, Japanese encephalitis virus, yellow fever virus, influenza virus or a poxvirus such as vaccinia virus.

Methods for infecting primary cells according to the second step of instant method for virus amplification are known. By way of example the virus may simply be added to the medium. Alternatively, the medium may be removed and the virus may be added to fresh medium, which in turn is added to the cells. To obtain an efficient infection the amount of the virus/medium suspension should be as low as possible to have a high virus concentration. After the attachment of the virus additional medium may be added.

In the third step of the instant method, the infected cells are cultivated in serum free medium until progeny virus is produced.

The serum free medium that is used in the second and third step of the method for the amplification of a virus may be the same medium that has already been used before, i.e. a serum free medium comprising a factor selected from growth factors and attachment factors, depending on the cell type. Alternatively, the serum free medium comprising growth factors and attachment factors may be removed at the step of infecting the primary avian cells with the virus, and/or at the step of cultivating the infected cells until virus progeny is produced, and replaced with a serum free medium which is essentially free of growth factors and attachment factors without adverse effects on the culture.

During all stages the medium may be supplemented with asparagine and/or glutamine as outlined above, wherein the total concentration of asparagine in the medium is as defined above.

The progeny virus may be concentrated and purified according to methods known to the person skilled in the art.

Thus, the present invention relates to a method for the amplification of a poxvirus comprising the following steps: (I) cultivating primary cells according to a method as described above, i.e. a method in which the primary cells are cultivated in serum free medium comprising a factor selected from the group consisting of growth factors and attachment factors, depending on the cell type, (II) infecting the primary cells with the poxvirus, (III) cultivating the infected cells in serum free medium until progeny virus is produced and (iv) isolating the virus from the infected cells. Viruses isolated according to the instant method are free of any products and/or infectious agents comprised in animal sera.

The process of passaging and/or further cultivating and/or plaque purifying and/or purifying by limited dilution or any other method under serum free conditions those viruses that previously have been or may have been amplified under serum containing conditions is termed "re-derivation". A re-derivation under serum-free conditions drastically reduces the risk of contaminations in the vaccine, in particular of undesired infectious agents.

The methods according to the present invention relate to cultivating primary avian cells and to amplifying a virus, wherein the virus is the virus that is to be re-derived. For example, the instant methods are useful for the re-derivation of viruses and virus stocks, in particular for stocks that have been, or may have been passaged in serum containing medium and/or with unclear passage histories.

One passage of the starting material, i.e. of the virus to be re-derived under serum free conditions, may be sufficient for the re-derivation of a virus. The term "passaging" refers to the steps of cultivating cells under serum free conditions, infection of the cells with the virus to be re-derived and obtaining the virus produced in the infected cells. Although one passage might be sufficient, it may be preferable to passage the virus several times under serum free conditions. In this case the virus obtained from the first passaging step is used to again infect fresh cells. The passaging under serum free conditions may be combined with one or more plaque purifications and/or with limited dilution and/or any other method for the purification of a virus under serum free conditions. The total number of passages, optionally by including plaque purification and/or limited dilution is in a range of 1 to more than 10, such as 3 to 8 or 4 to 6. The techniques of plaque purification and/or limited dilution are standard virological methods practiced by those skilled in the art.

The re-derivation according to the present invention may be done with a virus starting material that exhibits desired biological properties, wherein the virus used as starting material may have been amplified under serum containing conditions. After several passages under serum free conditions according to the present invention it is confirmed whether the virus passaged under serum free conditions is identical/similar to the virus originally passaged under serum containing methods. In most cases the virus obtained after the re-derivation has similar/identical properties to the virus used as starting material. There may also be situations in which the re-derived virus has even improved properties compared to the virus used as starting material, e.g. an improved safety profile.

The present invention also relates to the re-derived virus obtained by the method according to the present invention. The risk that poxvirus obtained by the re-derivation method according to the present invention comprises a BSE particle is less than $10^{32}$.

If it is intended to re-derive a virus, the following re-derivation plan may be used by way of example. This plan is particularly suitable for the re-derivation of a Vaccinia virus, e.g. an MVA strain that has or may have been cultivated under serum containing conditions: First the original Master Virus Bank (MVB) virus seed stock is re-cloned through, for example, 5 rounds of plaque purification by limited dilution (see example 9). Viruses from the original virus seed stock and from the new re-derived stock are compared both genetically and phenotypically. A genetic comparison of the virus cultivated under serum containing conditions and the re-derived virus may be made by, for example, (i) Restriction Enzyme mapping of the viral genome (RE-Map), (ii) PCR amplification of relevant parts of the genome such as the six deletion sites in case on MVA and/or (iii) PCR based restriction fragment length polymorphism mapping of the viral genome (PCR-RFLP Assay). A phenotypic characterization may, for example, be performed by: (i) comparing humoral responses in vaccinated mice, (ii) comparing efficacy using a lethal vaccinia model, (iii) evaluating safety by the vaccination of severely immune compromised mice, (iv) comparing the attenuation (replication) in a variety of mammalian cell lines.

The present invention consequently relates to a re-derivation process namely the method for the cultivation of primary avian cells as defined above and/or the method for the amplification of a virus as defined above, wherein the virus is the virus that is to be re-derived. The invention further relates to re-derived virus such as re-derived Vaccinia viruses, e.g. MVA strains such as MVA-BN. The re-derived virus can be e.g. a re-derived wild type virus, a re-derived attenuated virus or a re-derived recombinant virus. The invention further relates to compositions comprising re-derived virus.

The invention further relates to a virus including a re-derived virus, in particular to the viruses including the re-derived viruses as defined above as a medicament or vaccine. If the virus is a wild-type virus or an attenuated virus the virus can be used for vaccination against the virus as such. For this purpose attenuated viruses are particularly preferred. If the virus is a recombinant virus expressing proteins expressed from genes heterologous to the viral genome, it is possible to vaccinate against the virus as such and/or against the expressed heterologous protein. If the recombinant virus expresses a therapeutic gene such as an antisense RNA or a ribozyme the virus may be used as a medicament.

As discussed previously, it is understood by those skilled in the art that primary avian cells grow adversely under serum free conditions. The additional stress associated with a poxvirus infection may be expected to cause the already stressed cells to die before a significant amplification of the poxvirus occurs. Surprisingly, avian cells grown according to the present method, in a serum free medium comprising a factor selected from growth factors and attachment factors, effectively support viral replication and amplification of poxviruses.

The poxvirus is preferably an orthopoxvirus. Examples of *orthopox* viruses are avipoxviruses and vaccinia viruses.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

An example of a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in one-day old chickens. The strain is a commercial fowlpox virus vaccine strain designated 0 DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. The invention is preferably carried out with modified vaccinia virus Ankara (MVA) (Sutter, G. et al. [1994], Vaccine 12: 1032-40). Typical MVA strains are MVA 575 that has been deposited at the European Collection of Animal Cell Cultures under the deposition number ECACC V00120707 and MVA-572 deposited at ECACC under the deposition number V94012707. MVA-BN has been deposited at the European Collection of Animal Cell Cultures with the deposition number ECACC V00083008.

The virus to be amplified according to the method of the present invention may be a wild-type virus, an attenuated virus or a recombinant virus.

As pointed out above, for poxviruses the primary cells may be primary avian cells such as CEF cells or primary duck embryo fibroblasts. Again, one skilled in the art understands which primary cells are suitable for the amplification of which poxvirus. CEF cells are known for the amplification of MVA. If the method according to the present invention is used for the amplification of MVA in CEF cells, the starting pH of the medium may be in a range of about 7.0 to about 8.5. For MVA amplification in CEF cells in serum free medium, it is an aspect of the invention to select one or two of the factors selected from EGF and fibronectin.

The invention also relates to vaccinia virus strains obtained by the method of the present invention, in particular MVA-BN and its derivatives, which are further characterized by a failure to replicate in vivo. In the context of the present invention, "failure to replicate in vivo" refers to viruses that do not replicate in humans and in the mouse model described below. The "failure to replicate in vivo" can be determined in mice that are incapable of producing mature B and T cells. An example of such mice is the transgenic mouse model AGR129 (obtained from Mark Sutter, Institute of Virology, University of Zurich, Zurich, Switzerland). This mouse strain has targeted gene disruptions in the IFN receptor type I (IFN-α/β) and type II (IFN-γ) genes, and in RAG. Due to these disruptions, the mice have no IFN system and are incapable of producing mature B and T cells, and as such, are severely immune-compromised and highly susceptible to a replicating virus. In addition to the AGR129 mice, any other mouse strain may be used that is incapable of producing mature B and T cells, and as such, is severely immune-compromised and highly susceptible to a replicating virus. The viruses of the present invention do not kill AGR129 mice within a time period on the average of at least 45 days, and up to at least 60 days, and to 90 days post infection of the mice with $10^7$ pfu virus administered via intra-peritoneal injection. The viruses that exhibit "failure to replicate in vivo" are further characterized in that no virus can be recovered from organs or tissues of the AGR129 mice on the average of 45 days, 60 days, and even 90 days after infection of the mice with $10^7$ pfu virus administered via intra-peritoneal injection. Detailed information regarding the infection assays using AGR129 mice and the assays used to determine whether virus may be recovered from organs and tissues of infected mice can be found in the example section.

In a further embodiment, the vaccinia virus strains of the invention, in particular MVA-BN and its derivatives, are characterized as inducing a higher specific immune response compared to the strains MVA 575 and MVA 572, as determined in a lethal challenge mouse model. Briefly, in such a model unvaccinated mice die after infection with replication competent vaccinia strains such as the Western Reserve strain L929 TK+ or IHD-J. Infection with replication competent vaccinia viruses is referred to as "challenge" in the context of description of the lethal challenge model. Four days after the challenge, the mice are usually killed and the viral titer in the ovaries is determined by standard plaque assays using VERO cells (for more details see example section). The viral titer is determined for unvaccinated mice and for mice vaccinated with vaccina viruses of the present invention. More specifically, the viruses of the present invention are characterized in that, in this test after the vaccination with $10^2$ $TCID_{50}$/ml of virus of the present invention, the ovarian virus titers are reduced by at least an average of 70%, 80%, and even 90%, compared to unvaccinated mice.

In a further embodiment, the vaccinia viruses of the present invention, in particular MVA-BN and its derivatives, are useful for immunization with prime/boost administration of the vaccine. There have been numerous reports suggesting that prime/boost regimes using a known MVA as a delivery vector induce poor immune responses and are inferior to DNA-prime/MVA-boost regimes (Schneider et al., 1998, Nat. Med. 4; 397-402). In all of these studies the MVA strains that have been used are different from the vaccinia viruses of the present invention. To explain the poor immune response when MVA was used for prime and boost administration, it has been hypothesized that antibodies generated to MVA during the prime-administration neutralized the MVA administered in the second immunization, thereby preventing an effective boost of the immune response. In contrast, DNA-prime/MVA-boost regimes are reported to be superior in generating high avidity responses because this regime combines the ability of DNA to effectively prime the immune response with the properties of MVA to boost the response in the absence of a pre-existing immunity to MVA.

Clearly, if a pre-existing immunity to MVA and/or vaccinia prevents boosting of the immune response, then the use of MVA as a vaccine or therapeutic would have limited efficacy, particularly in the individuals that have been previously vaccinated against smallpox. However, the vaccinia virus of the present invention, in particular MVA-BN and its derivatives, as well as corresponding recombinant viruses harboring heterologous sequences, can be used to efficiently first prime and then boost immune responses in naive animals, as well as animals with a pre-existing immunity to poxviruses. Thus, the vaccinia virus of the present invention induces at least substantially the same level of immunity in vaccinia virus prime/vaccinia virus boost regimes compared to DNA-prime/vaccinia virus boost regimes.

The term "animal" as used in the present description is intended to also include human beings. Thus, the virus of the present invention is also useful for prime/boost regimes in human beings. If the virus is a non-recombinant virus such as MVA-BN or a derivative thereof, the virus may be used as a smallpox vaccine in humans, wherein the same virus can be used in both the priming and boosting vaccination. If the virus is a recombinant virus such as MVA-BN or a derivative thereof that encodes a heterologous antigen, the virus may be used in humans as a vaccine against the agent from which the heterologous antigen is derived, wherein the same virus can be used in both the priming and boosting vaccination.

A vaccinia virus is regarded as inducing at least substantially the same level of immunity in vaccinia virus prime/vaccinia virus boost regimes if, when compared to DNA-prime/vaccinia virus boost regimes, the CTL response, as measured in one of the following two assays ("assay 1" and "assay 2"), preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/29 vaccinia virus boost regimes. Most preferably, the CTL response is higher in both of the following assays.

Assay 1: For vaccinia virus prime/vaccinia virus boost administrations, 6-8 week old BALB/c (H-2d) mice are prime-immunized by intravenous administration with $10^7$ $TCID_{50}$ vaccinia virus of the invention expressing the murine polytope as described in Thomson et al., 1998, J. Immunol. 160, 1717 and then boost-immunized with the same amount of the same virus, administered in the same manner three weeks later. To this end, it is necessary to construct a recombinant vaccinia virus expressing the polytope. Methods to construct such recombinant viruses are known to a person skilled in the art and are described in more detail below. In DNA prime/vaccinia virus boost regimes the prime vaccination is done by intra muscular injection of the mice with 50 mg DNA expressing the same antigen as the vaccinia virus. The boost administration with the vaccinia virus is done in exactly the same way as for the vaccinia virus prime/vaccinia virus boost administration. The DNA plasmid expressing the polytope is also described in the publication referenced above, i.e., Thomson, et al. In both regimes, the development of a CTL response against the epitopes SYI, RPQ and/or YPH is determined two weeks after the boost administration. The determination of the CTL response is preferably done using the ELISPOT analysis as described by Schneider, et al., 1998, Nat. Med. 4, 397-402, and as outlined in the examples section below for a specific virus of the invention. The virus of the invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-γ producing cells/$10^6$ spleen cells (see also experimental section).

Assay 2: This assay basically corresponds to assay 1. However, instead of using $10^7$ $TCID_{50}$ vaccinia virus administered i.v., as in Assay 1; in Assay 2, $10^8$ $TCID_{50}$ vaccinia virus of the present invention is administered by subcutaneous injection for both prime and boost immunization. The virus of the present invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-γ producing cells/$10^6$ spleen cells (see also experimental section).

In summary, a representative vaccinia virus of the present invention is characterized by having at least one of the following properties:
- capability of reproductive replication in chicken embryo fibroblasts (CEF), but no capability of reproductive replication in a human cell line known to permit replication with known vaccinia strains,
- failure to replicate in vivo in those animals, including humans, in which the virus is used as a vaccine or active ingredient of a pharmaceutical composition,
- induction of a higher specific immune response compared to a known vaccinia strain,
- induction of at least substantially the same level of a specific immune response in vaccinia virus prime/vaccinia virus boost regimes when compared to DNA-prime/vaccinia virus boost regimes, and/or
- may or may not have the additional characteristic of reproductive replication in CEF cells grown in serum free medium.

Preferably, the vaccinia virus of the present invention has at least two of the above properties, and more preferably at least three of the above properties. Most preferred are vaccinia viruses having all of the above properties.

Representative vaccinia virus strains are MVA 575 deposited on Dec. 7, 2000 at the European Collection of Animal Cell Cultures (ECACC) with the deposition number V00120707; MVA-572 deposited at ECACC under the deposition number V94012707; and MVA-BN, deposited on Aug. 30, 2000, at ECACC with the deposition number V000083008, and derivatives thereof, in particular if it is intended to vaccinate/treat humans. MVA-BN and its derivatives are most preferred for humans.

In a further embodiment, the invention concerns a kit for vaccination comprising a virus of the present invention for the first vaccination ("priming") in a first vial/container and for a second vaccination ("boosting") in a second vial/container. The virus may be a non-recombinant vaccinia virus, i.e., a vaccinia virus that does not contain heterologous nucleotide sequences. An example of such a vaccinia virus is MVA-BN and its derivatives. Alternatively, the virus may be a recombinant vaccinia virus that contains additional nucleotide sequences that are heterologous to the vaccinia virus. As outlined in other sections of the description, the heterologous sequences may code for epitopes that induce a response by the immune system. Thus, it is possible to use the recombinant vaccinia virus to vaccinate against the proteins or agents comprising the epitope. The viruses may be formulated as shown below in more detail. The amount of virus that may be used for each vaccination has been defined above.

A process for obtaining a virus of the instant invention may comprise the following steps:
I. introducing a vaccinia virus strain, into non-human cells in which the virus is able to reproductively replicate, wherein the non-human cells are preferably selected from CEF cells,
II. isolating/enriching virus particles from these cells and
III. analyzing whether the obtained virus has at least one of the desired biological properties as previously defined above, wherein the above steps can optionally be repeated until a virus with the desired replication characteristics is obtained. The invention further relates to the viruses obtained by the method of the instant invention. Moreover, the invention pertains to such virus cultured in serum free media. Methods for determining the expression of the desired biological properties are explained in other parts of this description.

The growth behavior of the vaccinia viruses of the present invention, in particular the growth behavior of MVA-BN, indicates that the strains of the present invention are far superior to any other characterized MVA isolates in terms of attenuation in human cell lines and failure to replicate in vivo. The strains of the present invention are therefore ideal candidates for the development of safer products such as vaccines or pharmaceuticals, as described below.

In one further embodiment, the virus of the present invention, in particular MVA-BN and its derivatives, is used as a vaccine against human poxvirus diseases, such as smallpox.

In a further embodiment, the virus of the present invention may be recombinant, i.e., may express heterologous genes as, e.g., antigens or epitopes heterologous to the virus, and may thus be useful as a vaccine to induce an immune response against heterologous antigens or epitopes.

The term "immune response" means the reaction of the immune system when a foreign substance or microorganism enters the organism. By definition, the immune response is divided into a specific and an unspecific reaction although both are closely related. The unspecific immune response is the immediate defense against a wide variety of foreign substances and infectious agents. The specific immune response is the defense raised after a lag phase, when the organism is challenged with a substance for the first time. The specific immune response is highly efficient and is responsible for the fact that an individual who recovers from a specific infection is protected against this specific infection. Thus, a second infection with the same or a very similar infectious agent causes much milder symptoms or no symptoms at all, since there is already a "pre-existing immunity" to this agent. Such immunity and immunological memory persist for a long time, in some cases even lifelong. Accordingly, the induction of an immunological memory can be used for vaccination.

The "immune system" means a complex organ involved in the defense of the organism against foreign substances and microorganisms. The immune system comprises a cellular component, comprising several cell types, such as, e.g., lymphocytes and other cells derived from white blood cells, and a humoral component, comprising small peptides and complement factors.

"Vaccination" means that an organism is challenged with an infectious agent, e.g., an attenuated or inactivated form of the infectious agent, to induce a specific immunity. The term vaccination also covers the challenge of an organism with recombinant vaccinia viruses of the present invention, in particular recombinant MVA-BN and its derivatives, expressing antigens or epitopes that are heterologous to the virus. Examples of such epitopes are provided elsewhere in the description and include e.g., epitopes from proteins derived from other viruses, such as the Dengue virus, Hepatitis C virus, HIV, or epitopes derived from proteins that are associated with the development of tumors and cancer. Following administration of the recombinant vaccinia virus, the epitopes are expressed and presented to the immune system. A specific immune response against these epitopes may be induced. The organism, thus, is immunized against the agent/protein containing the epitope that is encoded by the recombinant vaccinia virus.

"Immunity" means partial or complete protection of an organism against diseases caused by an infectious agent due to a successful elimination of a preceding infection with the infectious agent or a characteristic part thereof. Immunity is based on the existence, induction, and activation of specialized cells of the immune system.

As indicated above, in one embodiment of the invention the recombinant viruses of the present invention, in particular recombinant MVA-BN and its derivatives, contain at least one heterologous nucleic acid sequence. The term "heterologous" is used hereinafter for any combination of nucleic acid sequences that is not normally found intimately associated with the virus in nature; such virus is also called a "recombinant virus".

According to a further embodiment of the present invention, the heterologous sequences are antigenic epitopes that are selected from any non-vaccinia source. The recombinant virus may express one or more antigenic epitopes from: *Plasmodium falciparum*, bacteria, including mycobacteria, influenza virus, viruses of the family of flaviviruses, paramyxoviruses, hepatitis viruses, human immunodeficiency viruses, or from viruses causing hemorrhagic fever, such as hantaviruses or filoviruses, i.e., ebola or marburg virus.

According to still a further embodiment, but also in addition to the above-mentioned selection of antigenic epitopes, the heterologous sequences may be selected from another poxyiral or a vaccinia source. These viral sequences can be used to modify the host spectrum or the immunogenicity of the virus.

In a further embodiment the virus of the present invention may code for a heterologous gene/nucleic acid expressing a therapeutic compound. A "therapeutic compound" encoded by the heterologous nucleic acid in the virus can be, e.g., a therapeutic nucleic acid, such as an antisense nucleic acid, including an antisense expression cassette or a ribozyme gene, or a peptide or protein with desired biological activity, or a gene coding for a peptide comprising at least one epitope to induce an immune response.

According to a further embodiment, the expression of a heterologous nucleic acid sequence may be, but not exclusively, under the transcriptional control of a poxvirus promoter, possibly a vaccinia virus promoter.

According to still a further embodiment, the heterologous nucleic acid sequence is inserted into a non-essential region of the virus genome. In another embodiment of the invention, the heterologous nucleic acid sequence is inserted at a naturally occurring deletion site of the MVA genome as disclosed in PCT/EP96/02926 the subject matter of which is hereby incorporated by reference. Methods for inserting heterologous sequences into the poxyiral genome are known to a person skilled in the art.

According to yet another embodiment, the invention also includes the genome of the virus, its recombinants, or functional parts thereof. Such viral sequences can be used to identify or isolate the virus or its recombinants, e.g., by using PCR, hybridization technologies, or by establishing ELISA assays. Furthermore, such viral sequences can be expressed from an expression vector to produce the encoded protein or peptide that then may supplement deletion mutants of a virus that lacks the viral sequence contained in the expression vector.

"Functional part" of the viral genome means a part of the complete genomic sequence that encodes a physical entity, such as a protein, protein domain, or an epitope of a protein. Functional part of the viral genome also describes parts of the complete genomic sequence that code for regulatory elements or parts of such elements with individualized activity, such as promoter, enhancer, cis- or trans-acting elements.

The recombinant virus of the present invention may be used for the introduction of a heterologous nucleic acid sequence into a target cell, the sequence being either homologous or heterologous to the target cell. The introduction of a heterologous nucleic acid sequence into a target cell may be used to produce in vitro heterologous peptides or polypeptides, and/or complete viruses encoded by the sequence. This method comprises the infection of a host cell with the recombinant MVA; cultivation of the infected host cell under suitable conditions; and isolation and/or enrichment of the peptide, protein and/or virus produced by the host cell.

Furthermore, the method for introduction of a homologous or heterologous sequence into cells may be applied for in vitro and preferably in vivo therapy. For in vitro therapy, isolated cells that have been previously (ex vivo) infected with the virus are administered to a living animal body for inducing an immune response. For in vivo therapy, the virus or its recombinants are directly administered to a living animal body to induce an immune response. In this case, the cells surrounding the site of inoculation are directly infected in vivo by the virus, or its recombinants, of the present invention.

Since the virus of the invention is highly growth restricted in human and monkey cells and thus, highly attenuated, it is ideal to treat a wide range of mammals, including humans. Hence, the present invention also provides a pharmaceutical composition and a vaccine, e.g., for inducing an immune response in a living animal body, including a human. The virus of the invention is also safe in any other gene therapy protocol.

A pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the virus or a recombinant of the present invention, is converted into a physiologically acceptable form. This can be done based on experience in the preparation of poxvirus vaccines used for vaccination against smallpox (as described by Stickl, H. et al. [1974] Dtsch. med. Wschr. 99, 2386-2392). For example, the purified virus is stored at −80° C. with a titer of $5\times10^8$ $TCID_{50}$/ml formulated in about 10 mM Tris, 140 mM NaCl, pH 7.4. For the preparation of vaccine shots, e.g., $10^2$-$10^8$ particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise, freeze-drying of the virus in a formulation. This formulation can contain additional additives such as mannitol, dextran, sugar, glycine, lactose, polyvinylpyrrolidone, or other additives, such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in 0.1 to 0.5 ml of an aqueous solution, preferably physiological saline or Tris buffer, and administered either systemically or locally, i.e., by parenteral, intramuscular, or any other path of administration known to a skilled practitioner. The mode of administration, dose, and number of administrations can be optimized by those skilled in the art in a known manner.

Additionally according to a further embodiment, the virus of the present invention is particularly useful to induce immune responses in immune-compromised animals, e.g., monkeys (CD4<400/μl of blood) infected with SIV, or immune-compromised humans. The term "immune-compromised" describes the status of the immune system of an individual that exhibits only incomplete immune responses or has a reduced efficiency in the defense against infectious agents. Even more interesting and according to still a further embodiment, the virus of the present invention can boost immune responses in immune-compromised animals or humans even in the presence of a pre-existing immunity to poxvirus in these animals or humans. Of particular interest, the virus of the present invention can also boost immune responses in animals or humans receiving an antiviral, e.g., antiretroviral therapy. "Antiviral therapy" includes therapeutic concepts in order to eliminate or suppress viral infection including, e.g., (i) the administration of nucleoside analogs, (ii) the administration of inhibitors for viral enzymatic activity or viral assembling, or (iii) the administration of cytokines to influence immune responses of the host.

According to still a further embodiment, the vaccine is especially, but not exclusively, applicable in the veterinary field, e.g., immunization against animal pox infection. In small animals, the immunizing inoculation is preferably administered by nasal or parenteral administration, whereas in larger animals or humans, a subcutaneous, oral, or intramuscular inoculation is preferred.

A vaccine shot containing an effective dose of only $10^2$ TCID$_{50}$ (tissue culture infectious dose) of the virus of the present invention is sufficient to induce complete immunity against a wild type vaccinia virus challenge in mice. This is particularly surprising since such a high degree of attenuation of the virus of the present invention would be expected to negatively influence and thereby, reduce its immunogenicity. Such expectation is based on the understanding that for induction of an immune response, the antigenic epitopes must be presented to the immune system in sufficient quantity. A virus that is highly attenuated and thus, not replicating, can only present a very small amount of antigenic epitopes, i.e., as much as the virus itself incorporates. The amount of antigen carried by viral particles is not considered to be sufficient for induction of a potent immune response. However, the virus of the invention stimulates, even with a very low effective dose of only $10^2$ TCID$_{50}$, a potent and protective immune response in a mouse/vaccinia challenge model. Thus, the virus of the present invention exhibits an unexpected and increased induction of a specific immune response compared to other characterized MVA strains. This makes the virus of the present invention and any vaccine derived thereof, especially useful for application in immune-compromised animals or humans.

According to still another embodiment of the invention, the virus is used as an adjuvant. An "adjuvant" in the context of the present description refers to an enhancer of the specific immune response in vaccines. "Using the virus as adjuvant" means including the virus in a pre-existing vaccine to additionally stimulate the immune system of the patient who receives the vaccine. The immunizing effect of an antigenic epitope in most vaccines is often enhanced by the addition of a so-called adjuvant. An adjuvant co-stimulates the immune system by causing a stronger specific immune reaction against an antigenic epitope of a vaccine. This stimulation can be regulated by factors of the unspecific immune system, such as interferon and interleukin. Hence, in a further embodiment of the invention, the virus is used in mammals, including humans, to activate, support, or suppress the immune system, and preferably to activate the immune response against any antigenic determinant. The virus may also be used to support the immune system in a situation of increased susceptibility to infection, such as in the case of stress.

The virus used as an adjuvant may be a non-recombinant virus, i.e., a virus that does not contain heterologous DNA in its genome. An example of this type of virus is MVA-BN. Alternatively, the virus used as an adjuvant is a recombinant virus containing in its genome heterologous DNA sequences that are not naturally present in the viral genome. For use as an adjuvant, the recombinant viral DNA preferably contains and expresses genes that code for immune stimulatory peptides or proteins such as interleukins.

According to a further embodiment, it is preferred that the virus is inactivated when used as an adjuvant or added to another vaccine. The inactivation of the virus may be performed by e.g., heat or chemicals, as known in the art. Preferably, the virus is inactivated by β-propriolacton. According to this embodiment of the invention, the inactivated virus may be added to vaccines against numerous infectious or proliferative diseases to increase the immune response of the patient to this disease.

EXPERIMENTAL PART

The present invention will be better understood in connection with the following examples, which are intended as an illustration of and not a limitation upon the scope of the invention.

Example 1

Preparation of Chicken Embryo Fibroblast (Cef) Cells

Specific pathogen free (SPF) fertilized eggs were stored not longer than 12 days at 4° C. The eggs were put into an incubator and incubated for 10-12 days at 37.8° C.±8° C. One petri dish per maximum 11 eggs was prepared with 10-20 ml PBS. The eggs were put in a dedicated egg carton and treated extensively with Bacillol® to sterilize the outside of the egg shell. After drying, a hole was made into the eggs and the shell was removed carefully. The chorioallantoic membrane was put aside. The embryos were lifted up by the feet and then their heads were cut off. The embryos were then transferred into the prepared petri dishes. After removing the feet the trunks were washed again with PBS. 11 trunks maximum were put into a 20 ml plastic syringe and squeezed into an Erlenmeyer flask. 5 ml of prewarmed (37° C.) Trypsin/EDTA-solution per trunk were added and the solution was stirred for 15 minutes with serum free medium at room temperature using a magnetic stirrer. Trypsinized cells were poured through a layer of mesh into a beaker. All cells were transferred to one 225 ml-centrifuge tube and centrifuged down at 20° C., 470×g for 7 minutes in a bench top centrifuge. After discarding the supernatant, the pellet was resuspended in 1 ml fresh pre-warmed (37° C.) serum free growth medium comprising 10 ng/ml EGF per trunk by pipetting up and down thoroughly. Fresh prewarmed (37° C.) serum free growth medium comprising 10 ng/ml EGF was added to a total volume of 150 ml. The centrifugation step was repeated. The supernatant was removed and the pellet was resuspended as described above. Fresh prewarmed (37° C.) serum free growth medium comprising 10 ng/ml EGF was added to a total volume of 100 ml. Cells were counted as described in the following section. The required amounts of cells were seeded in roller bottles with serum free growth medium comprising 10 ng/ml EGF and incubated at 37° C. Cells were ready for virus infection at day four after seeding.

Example 2

Counting Cell Density

A sample of the cell suspension (see section CEF preparation) was taken and mixed with one volume of Trypan blue, resulting in a final cell count of 20 to 100 cells per 16 small squares of a hemocytometer supplied by Fuchs-Rosenthal under the name of Hemocytometer Fast Read 102 (1:2-1:10 dilution). The sample was taken immediately after resuspending the cells in order to prevent reaggregation or sedimentation of the cells. After a few minutes of incubation time with Trypan blue in order to get the dye properly into dead cells, 10 µl of the cell suspension was added to the hemocytometer. Only white, living cells were counted under a light microscope using a 10× objective. In total, 3 representative big squares consisting of 3×16 small ones were counted. From every big square only two borders in L-Form were included in the counting. The average of counted cells was taken and the final cell concentration was calculated using the following formula: Average cell number×dilution×$10^4$=cells/ml. Finally the cell suspension was diluted to the desired working concentration.

Example 3

Effect of the Addition of a Factor Selected from Growth Factors and Fibronectin to a Serum Free Culture Medium on the Formation of a CEF-Monolayer In preliminary experiments it was shown that CEF cells do not attach to the surface of cell culture vessels if medium 199 is used that does not comprise FCS. Moreover, no monolayers are formed. Normal monolayer formation is observed if medium 199 containing 7% FCS is used. It was analyzed whether attachment and growth of CEF cells in serum free medium 199 can be achieved if recombinant Epidermal Growth Factor (rh-EGF) and Fibronectin (FN) are added to the medium.

For the experiments CEF cells were grown in medium 199 with the different additives alone or in combination. Cells grown in medium 199 without any additives served as negative control. Cells cultivated in medium 199 comprising 7% FCS served as positive control. All experiments were conducted in 6-well cell culture plates with 3 ml medium. The additives were treated according to the data sheets of the supplier before being used for the cell culture. Fibronectin was allowed to adsorb to the surface of the cell culture plates for 25 minutes before use. Fibronectin was used in a concentration of 3 µg/cm² and EGF was used in a concentration of 10 ng/ml. Before adding any cells the cell culture plates were brought into contact with the fibronectin-containing medium for 25 minutes.

Every culture medium plus the additives to be tested was cultured in duplicate. The 6-well cell culture plates were incubated for 4 days at 37° C. From day 1 to 4 the attachment and growth of the cells was evaluated using a microscope.

For the positive control a normal attachment and growth of the CEF cells has been observed. For Medium 199 without additives nearly no attachment of CEF cells could be observed.

A crucial improvement in the forming of a monolayer was seen by the use of EGF added to Medium 199 compared to Medium 199 without additives. It was found that the cells attached and formed the typical fibroblast morphology. Furthermore, a continuous growth could be observed over the whole period of 4 days.

An improvement of cell attachment was also achieved by adding fibronectin to the culture medium. The addition of both, EGF and Fibronectin resulted in a slight improvement compared to the addition of EGF only and Fibronectin only.

In summary, monolayer formation of CEF cells in the serum-free Medium 199 can be supported by the use of the additives EGF and Fibronectin.

Moreover, in parallel sets of experiments 1×$10^7$ CEF cells were seeded in medium comprising 10% FCS, medium not comprising FCS and medium not comprising FCS but comprising EGF. The cell number was counted 2 days after seeding. The number of cells amounted to 42%, 6% and 44%, respectively, of the cell number used for seeding. Thus, the results for the cells seeded in serum free medium comprising EGF were as good as the results obtained with medium comprising FCS and significantly better than with medium neither containing serum nor EGF.

In addition the medium comprising EGF was compared to various standard serum free media, such as DMEM, Opti-Mem or 293-SFM. To this end 1×$10^7$ CEF cells were seeded in the various serum-free media and cultivated for 4 days. The number of cells cultivated in medium comprising EGF was 24, 5 and 12 times higher than the number of cells cultivated in serum free DMEM, Opti.Mem and 293-SFM, respectively.

Example 4

Infection of CEF Cells with MVA

CEF cells were infected four days after seeding in roller bottles. At that time point cells have grown to an adequate monolayer. Cells were infected with a MOI of 1 or 0.1 MVA. For the infection the growth medium was removed from the flasks. The desired amount of virus per roller bottle was diluted in 20 ml of the appropriate infection medium without serum. At this stage the serum free medium may or may not comprise a factor selected from growth factors and fibronectin. Cells were incubated with the virus for 1 hour at 37° C. at 0.3-0.5 rpm in a roller bottle incubator. After 1 hour the roller bottles were filled with the appropriate serum free growth medium to a total volume of 200 ml per roller bottle. At this stage the serum free medium may or may not comprise a factor selected from growth factors and fibronectin. Virus replication was stopped after 48 or 72 hours by freezing the roller bottles to −20° C.

Example 5

Preparation of Viral Extracts from Infected CEF Cells and Titration of MVA

The frozen roller bottles were thawed at room temperature. During the thawing process the cells detach from the surface of the roller bottles and can mechanically be removed by shaking the flasks. Virus/cell suspension was harvested and aliquoted to smaller volumes. To release the virus from the infected cells, virus/cell suspensions were 3 times freeze/thawed. The freeze/thawed virus samples were used for titration.

Titrations were performed on 1st passage CEF cells in 96-well plates, using 10-fold dilutions of viral suspension and 8 replicates per dilution. After the infection, infected cells were visualized with an anti-vaccinia virus antibody and an appropriate staining solution.

In detail, at day zero of the assay primary CEF cells (see section "preparation of Chicken Embryo Fibroblast (CEF) cells") were trypsinized and counted as described in the section "counting cell density". The cells were diluted to $1 \times 10^5$ cells/ml in RPMI medium with 7% FCS. Following this dilution, 100 µl were seeded in each well of the 96-well plates using a multichannel pipette. Cells were incubated over night at 37° C. and 5% $CO_2$. The virus samples to be titrated (see section "preparation of viral extracts from infected CEF cells) were serially diluted in 10-fold steps from $10^{-1}$-$10^{-12}$ using RPMI without serum. This serial dilution is carried out by adding 900 µl RPMI to all the wells of a 96-deep-well plate. 100 µl of virus sample was added to all the wells of the first row and mixed. Thereafter, 100 µl of each sample were transferred to the next row of wells using a multi-channel pipette. The 96-deep-well plates were kept on ice when performing the dilutions. Plates were incubated for 5 days at 37° C. and 5% $CO_2$ to allow the infection to proceed. After 5 days, cells were immunohistochemically stained with a vaccinia virus specific antibody. For the staining, the culture medium was removed by turning the 96-well plate upside down over a receptacle. Cells were fixed with 100 µl/well methanol/acetone (1:1) mixture for 10 minutes at room temperature. The fixing solution was removed and plates were air-dried. After drying, cells were washed once with PBS and incubated for 1 hour at room temperature with the anti-vaccinia virus antibody (Anti-Vaccinia virus antibody, rabbit polyclonal, IgG fraction (Quartett, Berlin, Germany #9503-2057) diluted to 1:1000 in PBS with 3% FCS. After removing the antibody, cells were washed twice with PBS and incubated for 1 hour at room temperature with HRP-coupled (Horseradish Peroxidase-coupled) anti-rabbit antibody (Anti-rabbit IgG antibody, HRP-coupled goat polyclonal (Promega, Mannheim, Germany #W4011) diluted to 1:1000 in PBS with 3% FCS. Again, cells were washed with PBS and stained either with o-Dianisidine or TMB. For using the o-Dianisidine staining method, cells were incubated with 100 µl/well staining solution consisting of 5 mg o-Dianisidine and 180 µl 30% $H_2O_2$ per 60 ml of 50 mM phosphate-citrate buffer. Cells were incubated at room temperature until they stained brown. Infected cells were clearly visible after 1-3 hours. Using the TMB staining method, cells were incubated with 30 µl/well 1.2 mM TMB (Seramun Diagnostica GmbH). After 15 minutes incubation time, the TMB solution was removed and cells were washed once with PBS. Infected cells appear dark blue. The plates were scored for infected cells. The viral titer was calculated using the formula of Spearman and Kaerber. For the calculation of the $TCID_{50}$ every well showing brown or blue cells was marked positive. Because assay parameters are kept constant, the following simplified formula was used:

Virus titer$[TCID_{50}/ml]=10^{[a+1.5+xa/8+xb/8+xc/8]}$     i.

b. a=dilution factor of last column, in which all eight wells are positive
   c. $x_a$=number of positive wells in column a+1
   d. $x_b$=number of positive wells in column a+2
   e. $x_c$=number of positive wells in column a+3

Example 6

Optimal Seeding Density for CEF Cells in Serum Free Medium and Optimal Amount of MVA for Infection of CEF Cells An optimal seeding cell density of $7.5 \times 10^7$ cells/850 $cm^2$ (surface of one roller flask) was determined for serum-free CEF growth. Cells were able to build a good monolayer without forming big clumps at day four after seeding and could be infected at this time point.

Experiments were carried out to determine the best level of viral inoculation and length of the infection for the maximum production of MVA from CEF cells cultured in a serum-free process. CEF cells were seeded at a density of $7.5 \times 10^7$ cells/ 850 $cm^2$ in medium according to the present invention. At day 4 after seeding, cells were infected with different amounts of MVA in the range of 0.05 to 1.0 $TCID_{50}$/cell of MVA. Best results were obtained with 0.1 $TCID_{50}$/cell of MVA.

Example 7

Optimal pH of Serum Free Medium for Culturing and Infection with MVA

MVA and other poxvirus infections are sensitive pH below 7.0. Poxviruses are not stable at acid pH and it is recommended that purified poxviruses are stored in a buffered solution above pH 7.0 to ensure stability and viral integrity upon storage as a liquid viral preparation. Experiments were carried out to determine the effect on virus yield when carrying out infection at different starting pH. Roller bottles were seeded with CEF cells in the usually way in serum free medium comprising 10 ng/ml EGF plus 4 mM L-glutamine and cultured for 4 days. Cells were infected with MVA at 0.1 $TCID_{50}$/cell in serum free medium comprising 10 ng/ml EGF plus L-glutamine and 1 mM asparagine at different pH's ranging from 6.5 to 9.0. At 72 hours post infection, the pH of the medium was measured and viral yields were determined by titrating cell extracts in the usual manner. The results are presented in the following table, which shows the effect of initial pH of the medium at the start of the infection on virus yield.

| | serum free medium comprising 10 ng/ml EGF | |
|---|---|---|
| Starting pH | pH at 72 h p.i. | Titer [$TCID_{50}$/ml] |
| 6.5 | 7.05 | $0.56 \times 10^7$ |
| 7.0 | 7.34 | $10.0 \times 10^7$ |
| 7.5 | 7.53 | $5.60 \times 10^7$ |
| 8.0 | 7.68 | $8.60 \times 10^7$ |
| 8.5 | 7.75 | $7.80 \times 10^7$ |
| 9.0 | 8.03 | $0.65 \times 10^7$ |

For the infections carried out in serum free medium comprising 10 ng/ml EGF supplemented with L-glutamine and asparagine, the viral production was relatively constant with a starting pH from 7.0 to 8.5 but viral productions were low at starting pH of 6.5 and 9.0. Best yield was obtained at starting pH 7.0. Commercially available standard serum free media usually have a pH of 7.4. Therefore adjusting the pH of the serum free medium to 7.0 can help to improve virus yield.

Example 8

Effect of Added Asparagine to the Serum Free Medium

Preliminary experiments have revealed that the amount of asparagine may be limiting during the cultivation of CEF cells and the infection of CEF cells with MVA. To overcome the depletion of asparagine in the serum free media during the culturing and infection process, extra asparagine was added to the medium as a supplement before infecting CEF cells. To determine the optimal amount of asparagine to supplement the medium with, roller bottles were seeded with CEF cells ($7.5 \times 10^7$ cells/850 cm$^2$) in serum free medium comprising 10 ng/ml EGF plus 4 mM L-glutamine. Four days after seeding cells were infected with MVA at 0.1 TCID$_{50}$/cell in serum free medium comprising 10 ng/ml EGF plus 4 mM L-glutamine supplemented with different asparagine concentrations (0.5, 1.0 and 1.5 mM). Viral replication was stopped at 72 hours post infection and viral titers were determined. The results are shown in the following table that shows the production of MVA from CEF cells supplemented with different levels of asparagine for the infection stage. The titers represent the averages of 3 roller bottles per asparagine supplementation.

| Supplement Asparagine | Viral titers after 72 hours infection [TCID$_{50}$/ml] |
|---|---|
| 0.0 mM | $1.8 \times 10^8$ |
| 0.5 mM | $1.3 \times 10^8$ |
| 1.0 mM | $6.8 \times 10^8$ |
| 1.5 mM | $1.0 \times 10^8$ |

The results demonstrate that supplementing the serum free medium comprising 10 ng/ml EGF medium with asparagine could improve viral production and that supplementation to 1 mM for the infection process was optimal.

Example 9

Re-Derivation of Viruses

It is the aim of this example to show the usefulness of the methods according to the present invention for the re-derivation of viruses. We therefore intentionally cultivate MVA-BN under standard serum containing conditions. Accordingly, such vaccine may potentially comprise undesired viral contaminants or infectious agents such as BSE. The virus obtained after cultivation under serum containing conditions is then used as starting material for the re-derivation of the virus under serum free conditions according to methods described in the present application to obtain a re-derived virus stock wherein the risk of said virus to contain a BSE particle is less than $10^{32}$.

MVA-BN virus seed stock: The starting material for a re-derived MVA-BN virus seed stock is an inoculate obtained by intentionally cultivating MVA-BN under standard serum containing conditions (10% fetal calf serum).

Primary CEF Cells: Primary CEF cells are prepared from certified SPF eggs as outlined below. Certified fertilised SPF eggs are supplied by Charles River SPAFAS. The flocks at Charles River are tested according to European Pharmacopoeia section 5.2.2 (REF 12.4). Upon arrival the package and the eggs are checked visually for damage and dirt. Damaged eggs are removed. The eggs are stored refrigerated for not longer than 12 days at +2° C. to 8° C. Before incubation the eggs are disinfected by spraying with Mel Sept and put into an egg incubator. Incubation is performed for 10 to 12 days (preferable 11 days) at 37.8° C.+/−0.8° C. and 60%+/−10% relative humidity.

Prior to cell preparation the eggs are transferred to a dedicated egg carton and extensively treated with Mel Sept by spraying. The eggs are allowed to dry under a laminar flow.

The eggs are opened and the embryos are removed. Dead embryos and embryos showing deformations are excluded.

The heads and feet of the embryos are cut off.

Trunks are homogenised mechanically by squeezing them in a plastic syringe.

Cells are incubated at room temperature with Trypsin/EDTA solution while stirring.

Homogenised cells are poured through one layer of mesh and collected.

The homogenised cells are centrifuged. The supernatant is discarded and the cell sediment is washed with a serum free medium according to the present invention.

The cells are pelleted again by centrifugation.

The supernatant is discarded and the cells are re-suspended in a serum free medium according to the present invention.

Cells are counted and immediately seeded in a serum free medium in appropriate culture vessels.

Plaque purification and final amplification of selected clone: The 5 rounds of plaque purification by limited dilution are conducted.

Seeding of Cells:

Primary CEF cells are seeded in a T175 flask ($1 \times 10^7$ cells/flask) in a serum free medium according to the present invention and incubated at 37° C.+/−2° C. for 3 to 8 days.

First passage CEF cells are seeded in 96 well plates (1-2× $10^5$ cells/ml) using a serum free medium according to the present invention and incubated for 24 h at 37° C.+/−2° C.

Approximately 10 plates are used per round of plaque purification.

Infection of Cells:

10 fold serial virus dilutions ($10^{-1}$ to $10^{-10}$) are prepared in a serum free medium according to the present invention. 100 µl of the virus dilution/well are transferred to the 96 well plates containing CEF cells.

The plates are incubated for 5 to 6 days at 37° C.+/−2° C.

Isolation of Plaques:

Single virus plaques are visually detected under a microscope. 5 to 10 single plaques are collected per round of plaque purification.

Each plaque is harvested using a pipette tip by scrapping and transferred to a 1.5 ml tube. The volume is adjusted to 200 µl with a serum free medium according to the present invention.

The virus is released from the harvested cells by three cycles of freeze-thawing: freeze tube in liquid Nitrogen or at −80° C., thaw at room temperature, repeat procedure twice.

The virus suspension can be stored at −80° C. until further analysis. Alternatively if only one single virus plaque is detected per well, cells can be harvested by freeze-thawing the whole 96 well plate three-times.

For amplification, 100 µl of the virus suspension is transferred to cells grown in 12 well plates.

Amplification of Virus on 12 Well Plates:

First passage CEF cells are seeded in 12 well plates ($5 \times 10^4$ cells/cm$^2$) in 1 ml of a serum free medium according to the present invention and incubated for 24 h at 37° C.+/−2° C.

Cells show 80 to 100% confluence for infection.

100 µl of the virus suspension are added/well.

Cells are incubated for 48 to 72 h.

After 48 to 72 h the medium is removed and 300 µl of PBS per well are added. Cells are harvested in PBS and transferred to a 1.5 ml tube. If cells are already detached they are harvested (by scraping) directly in the media and transferred to a 1.5 ml tube.

The virus is released from the harvested cells by three cycles of freeze-thawing: freeze tube in liquid Nitrogen or at −80° C., thaw at room temperature, repeat procedure twice.

The virus suspension can be stored at −80° C. until further analysis.

Screening of Amplified Virus:

200 µl of the solution are used for DNA preparation and PCR screening.

The remaining 100 µl are used for the next plaque purification round.

Final amplification of selected clone: After 5 rounds of plaque purification, the final selected clone is further amplified to obtain enough material to produce a new master seed. The minimal amount of virus needed for production of a new master seed is $1\times10^8 TCID_{50}$ in 16-20 ml. The selected clone (already amplified on a 12 well plate) is transferred to a T25 cell culture flask for amplification. The cell virus suspension is harvested by three cycles of freeze-thawing. The virus suspension is then transferred to a T75 cell culture flask for amplification and harvested. The virus is released by 3 cycles of freeze-thawing. Final amplification is performed in 3 to 5 T175 cell culture flasks. Material from 3 to 5 T175 flasks is harvested and subjected to 3 cycles of freeze-thawing. The virus suspension is titrated, checked for sterility and tested for identity by PCR analysis of the 6 deletion sites.

Production of new master seed: Primary CEF cells are seeded in roller bottles (850 cm$^2$) with $7.5\times10^7$ CEF cells in 200 ml of a serum free medium according to the present invention. 2 to 5 roller bottles are seeded and incubated for 4 days at 37° C.+/−2° C., 0.3 rpm (±0.2 rpm) in a roller incubator. A virus suspension is prepared with a final titer of $1.0\times1\times10^6 TCID_{50}$ (±0.5 log) in RPMI media. 10 ml are needed per roller bottle. This corresponds to an MOI of 0.1. The medium is removed from the roller bottles. 10 ml of the virus suspension is added to each roller bottle and incubated for 1-3 hrs in a roller incubator. 140 ml RPMI are added and incubated for 72 hours (±8 hours), 0.5 rpm (±0.2 rpm).

Bottles are checked macroscopically for microbial contamination. The roller bottles are transferred into a −20° C. freezer, and the cell/virus suspension is allowed to freeze. The roller bottles are stored at room temperature until the suspension has started to thaw and remove cells from the wall by shaking thoroughly. The cell/virus suspension is allowed to thaw completely. The cell/virus suspension is harvested into an appropriate vessel and aliquot a 4.5 ml in 5 ml cryotubes. Approximately 100 vials can be obtained from one roller bottle. Filled virus suspension is stored at −20° C.

Example 10

Growth Kinetics of a Strain of MVA Cultured in Serum Free Medium in Selected Cell Lines and Replication In Vivo Growth kinetics in cell lines: To characterize a newly isolated strain of the present invention (further referred to as MVA-BN) which is cultured in serum free media, the growth kinetics of the new strain are compared to those of known MVA strains that have already been characterized.

The experiment compares the growth kinetics of the following viruses in the subsequently listed primary cells and cell lines:
 a. MVA-BN
 b. MVA as characterized by Altenburger (U.S. Pat. No. 5,185,146) and further referred to as MVA-HLR;
 c. MVA (passage 575) as characterized by Anton Mayr (Mayr, A., et al., [1975] Infection 3; 6-14) and further referred to as MVA-575 (ECACC V00120707);
 d. MVA (passage 572) and further referred to as MVA-572 (ECACC V94012707); and
 e. MVA-Vero as characterized in the International Patent Application PCT/EP01/02703 (WO 01/68820); Virus stock, passage 49, #20, 22.03.99 crude, titered at $4.2\times 10^7 TCID_{50}$/ml.

The primary cells and cell lines used are:
 a. CEF Chicken embryo fibroblasts (freshly prepared from SPF eggs);
 b. HeLa Human cervix adenocarcinoma (epithelial), ATCC No. CCL-2;
 c. 143B Human bone osteosarcoma TK-, ECACC No. 91112502;
 d. HaCaT Human keratinocyte cell line, Boukamp et at. 1988, J Cell Biol 106(3): 761-771;
 e. BHK Baby hamster kidney, ECACC 85011433;
 f. Vero African green monkey kidney fibroblasts, ECACC 85020299;
 g. CV1 African green monkey kidney fibroblasts, ECACC 87032605.

For infection the cells are seeded onto 6-well-plates at a concentration of $5\times10^5$ cells/well and incubated overnight at 37° C., 5% $CO_2$ in DMEM (Gibco, Cat. No. 61965-026) with 2% FCS. The cell culture medium is removed and cells are infected at approximately moi 0.05 for one hour at 37° C., 5% $CO_2$ (for infection it is assumed that cell numbers doubled over night). The amount of virus used for each infection is $5\times10^4 TCID_{50}$ and is referred to as Input. The cells are then washed 3 times with DMEM and finally 1 ml DMEM, 2% FCS is added and the plates are left to incubate for 96 hours (4 days) at 37° C., 5% $CO_2$. The infections are stopped by freezing the plates at −80° C.; followed by titration analysis.

Titration Analysis (Immunostaining with a Vaccinia Virus Specific Antibody):

For titration of amount of virus test cells (CEF) are seeded on 96-well-plates in RPMI (Gibco, Cat. No. 61870-010), 7% FCS, 1% Antibiotic/Antimycotic (Gibco, Cat. No. 15240-062) at a concentration of $1\times10^4$ cells/well and incubated over night at 37° C., 5% $CO_2$. The 6-well-plates containing the infection experiments are frozen/thawed 3 times and dilutions of $10^{-1}$ to $10^{-12}$ are prepared using RPMI growth medium. Virus dilutions are distributed onto test cells and incubated for five days at 37° C., 5% $CO_2$ to allow CPE (cytopathic effect) development. Test cells are fixed (Acetone/Methanol 1:1) for 10 min, washed with PBS and incubated with polyclonal vaccinia virus specific antibody (Quartett Berlin, Cat. No. 9503-2057) at a 1:1000 dilution in incubation buffer for one hour at RT. After washing twice with PBS (Gibco, Cat. No. 20012-019) the HRP-coupled anti-rabbit antibody (Promega Mannheim, Cat. No. W4011) is added at a 1:1000 dilution in incubation buffer (PBS containing 3% FCS) for one hour at RT. Cells are again washed twice with PBS and incubated with staining solution (10 ml PBS+ 200 µl saturated solution of o-dianisidine in 100% ethanol+15 µl $H_2O_2$ freshly prepared) until brown spots are visible (two hours). Staining solution is removed and PBS is added to stop the staining reaction. Every well exhibiting a brown spot is marked as positive for CPE and the titer is calculated using the formula of Kaerber ($TCID_{50}$ based assay) (Kaerber, G. 1931. Arch. Exp. Pathol. Pharmakol. 162, 480).

Cell preparations are infected with investigational viruses as defined above with the exception that MVA-BN is cultured in serum free media and the other investigational viruses are not cultured in serum free media and incubated for 96 hours. The infections are stopped by freezing at −80° C., followed by titration analysis as described above.

Investigational viruses amplify well in CEF cells. In Vero and CV1 cells, MVA-BN is distinguished for not amplifying well in these cells. In human cells 143B, HeLa and HaCaT, MVA-BN is distinguished for being the only investigational virus to demonstrate complete attenuation, exhibiting a significant decrease over input. Consequently, it is demonstrated that MVA-BN cultivated in a serum free environment exhibits critical attenuation over other known MVA cultivated in a variety of animal and human cell lines.

The viruses are used to infect duplicate sets of cells that are expected to be permissive for MVA (i.e., CEF and BHK) and cells expected to be non-permissive for MVA (i.e., CV-1, Vero, Hela, 143B and HaCaT). The cells are infected at a low multiplicity of infection, i.e., 0.05 infectious units per cell ($5 \times 10^4$ TCID$_{50}$). The virus inoculum is removed and the cells are washed three times to remove any remaining unadsorbed viruses. Infections are left for a total of 4 days when viral extracts are prepared and then titered on CEF cells.

It is demonstrated that all viruses amplified well in CEF cells as expected, since this is a permissive cell line for all MVAs. Additionally, it is demonstrated that all viruses amplified well in BHK (Hamster kidney cell line). MVA-Vero performs the best, since BHK is a permissive cell line for this strain.

Concerning replication in Vero cells (Monkey kidney cell line), MVA-Vero amplifies well, as expected. MVA-HLR, MVA-575 and MVA-572 amplify well with a significant increase above Input. Only MVA-BN is found to not amplify as well in these cells when compared to the other strains.

Also concerning replication in CV1 cells (Monkey kidney cell line) it is found that MVA-BN is highly attenuated in this cell line. It exhibits a 200-fold decrease below Input. MVA-575 does not amplify above the Input level and also exhibits a slight negative amplification. MVA-HLR amplifies the best with a significant increase above Input, followed by MVA-Vero and MVA-572.

It is most interesting to compare the growth kinetics of the various viruses in human cell lines. Regarding reproductive replication in 143B cells (human bone cancer cell line) it is demonstrated that MVA-Vero is the only strain to show amplification above Input. All other viruses do not amplify above Input, however there is a big difference between the MVA-HLR and MVA-BN, MVA-575 and MVA-572. MVA-HLR is "borderline", whereas MVA-BN exhibits the greatest attenuation, followed by MVA-575 and MVA-572. To summarize, MVA-BN is superior with respect to attenuation in human 143B cells.

Furthermore, concerning replication in HeLa cells (human cervix cancer cells) it is demonstrated that MVA-HLR amplifies well in this cell line, and even better than it did in the permissive BHK cells. MVA-Vero also amplified in this cell line. However, MVA-BN, and also to a lesser extent MVA-575 and MVA-572, are attenuated in these cell lines.

Concerning the replication in HaCaT cells (human keratinocyte cell line), it is demonstrated that MVA-HLR amplifies well in this cell line. MVA-Vero adapted and MVA-575 and MVA-572 exhibit amplification in this cell line. However, MVA-BN is the only one to demonstrate attenuation).

From this experimental analysis, we may conclude that MVA-BN is the most attenuated strain in this group of viruses. MVA-BN demonstrates extreme attenuation in human cell lines. Thus, MVA-BN is the only MVA strain exhibiting an amplification ratio of less than 1 in each human cell line examined, i.e., 143B, Hela, HaCaT, and 293.

MVA-575 exhibits a profile similar to that of MVA-BN, however it is not as attenuated as MVA-BN.

MVA-572 is less attenuated than MVA-575.

MVA-HLR amplifies well in all (human or otherwise) cell lines tested, except for 143B cells. Thus, it is regarded as replication competent in all cell lines tested, with the exception of 143B cells. In one case, it even amplifies better in a human cell line (HeLa) than in a permissive cell line (BHK).

MVA-Vero does exhibit amplification in all cell lines, but to a lesser extent than demonstrated by MVA-HLR (ignoring the 143B result). Nevertheless, it cannot be considered as being in the same "class" with regards to attenuation, as MVA-BN or MVA-575.

Example 11

Replication In Vivo

Given that some MVA strains clearly replicate in vitro, different MVA strains are examined with regard to their ability to replicate in vivo using a transgenic mouse model AGR129. This mouse strain has targeted gene disruptions in the IFN receptor type I (IFN-$\alpha/\beta$) and type II (IFN-$\gamma$) genes, and in RAG. Due to these disruptions, the mice have no IFN system and are incapable of producing mature B and T cells and, as such, are severely immune-compromised and highly susceptible to a replicating virus. Groups of six mice are immunized (i.p) with $10^7$ pfu of either MVA-BN, which is cultured in serum free media, MVA-HLR, MVA-572 (used in 120,000 people in Germany) or MVA-575 and monitored daily for clinical signs. All mice vaccinated with MVA-HLR or MVA-572 die within several weeks. At necropsy, there are general signs of severe viral infection in the majority of organs. A standard plaque assay measures the recovery of MVA ($10^8$ pfu) from the ovaries. In contrast, mice vaccinated with the same dose of MVA-BN (corresponding to the deposited strain ECACC V00083008) survive for more than 90 days and no MVA-BN is recovered from organs or tissues.

When taken together, data from the in vitro and in vivo studies clearly demonstrate that MVA-BN cultured in serum free media is more highly attenuated than the parental and commercial MVA-HLR strain, as well as MVA-575 and MVA-572, and may be safe for administration to immune-compromised subjects.

Example 12

Immunological and In Vivo Data in Animal Model Systems

These experiments are designed to compare different dose and vaccination regimens of MVA-BN compared to other MVAs in animal model systems.

Different Strains of MVA Differ in their Ability to Stimulate the Immune Response:

Replication competent strains of vaccinia induce potent immune responses in mice and at high doses are lethal. Although MVA are highly attenuated and have a reduced ability to replicate on mammalian cells, there are differences in the attenuation between different strains of MVA. Indeed, MVA-BN appears to be more attenuated than other MVA strains, even the parental strain MVA-575. To determine whether this difference in attenuation affects the efficacy of MVA to induce protective immune responses, different doses of MVA-BN which is cultured in serum free medium and MVA-575 or MVA-572 are compared in a lethal vaccinia challenge model. The levels of protection are measured by a reduction in ovarian vaccinia titers determined 4 days post challenge, as this allows a quantitative assessment of different doses and strains of MVA.

Lethal Challenge Model

Specific pathogen-free 6-8-week-old female BALB/c (H-2d mice (n=5) are immunized (i.p.) with different doses ($10^2$, $10^4$ or $10^6$ TCID$_{50}$/ml) of either MVA-BN which is cultured in serum free medium, MVA-575 or MVA-572. MVA-BN, MVA-575 and MVA-572 are propagated on CEF cells (MVA-BN being propagated in serum free media), and are sucrose purified and formulated in Tris pH 7.4. Three weeks later the mice receive a boost of the same dose and strain of MVA, which is followed two weeks later by a lethal challenge (i.p.) with a replication competent strain of vaccinia. As replication competent vaccinia virus (abbreviated as "rVV") either the strain WR-L929 TK+ or the strain IHD-J are used. Control mice receive a placebo vaccine. The protection is measured by the reduction in ovarian titers determined 4 days post challenge by standard plaque assay. For this, the mice are sacrificed on day 4 post the challenge and the ovaries are removed, homogenized in PBS (1 ml) and viral titers determined by standard plaque assay using VERO cells (Thomson, et al., 1998, J. Immunol. 160: 1717).

Mice vaccinated with two immunizations of either $10^4$ or $10^6$ TCID$_{50}$/ml of MVA-BN which is cultured in serum free medium, MVA-575 or MVA-572 are completely protected as judged by a 100% reduction in ovarian rVV titers 4 days post challenge. The challenge virus is cleared. However, differences in the levels of protection afforded by MVA-BN, MVA-575 or MVA-572 are observed at lower doses. Mice receiving two immunizations of $10^2$ TCID$_{50}$/ml of MVA 575 or MVA-572 fail to be protected, as judged by high ovarian rVV titers. In contrast, mice vaccinated with the same dose of MVA-BN exhibit a significant reduction in ovarian rVV titers. The control mice receiving a placebo vaccine have a mean viral titer of $5.11 \times 10^7$ pfu ($+/- 3.59 \times 10^7$).

All strains of MVA induce protective immune responses in mice against a lethal rVV challenge. Although all strains of MVA are equally efficient at higher doses, differences in their efficacy are clearly evident at sub-optimal doses. MVA-BN which is cultured in serum free medium is more potent than its parent strain MVA-575 or MVA-572 at inducing a protective immune response against a lethal rVV challenge, which may be related to the increased attenuation of MVA-BN compared to MVA-575 and MVA-572.

Example 13

MVA-BN in Prime/Boost Vaccination Regimes

Induction of Antibodies to MVA Following Vaccination of Mice with Different Smallpox Vaccines The efficacy of MVA-BN which is cultured in serum free medium is compared to other MVA and vaccinia strains previously used in the eradication of smallpox. These include single immunizations using the Elstree and Wyeth vaccinia strains produced in CEF cells and given via tail scarification, and immunizations using MVA-572 that was previously used in the smallpox eradication program in Germany or MVA-575. In addition, MVA-BN, MVA 572 and MVA-575 are compared as a pre-vaccine followed by Elstree via scarification. For each group eight BALB/c mice are used and all MVA vaccinations ($1 \times 10^7$ TCID$_{50}$) are given subcutaneously at week 0 and week 3. Two weeks following the boost immunization the mice are challenged with vaccinia (IHD-J) and the titers in the ovaries are determined 4 days post challenge. All vaccines and regimes induce 100% protection.

The immune responses induced using these different vaccines or regimes are measured in animals prior to challenge. Assays to measure levels of neutralizing antibodies, T cell proliferation, cytokine production (IFN-γ vs IL-4) and IFN-γ production by T cells are used. The level of the T cell responses induced by MVA-BN, as measured by ELISPOT, is generally equivalent to other MVA and vaccinia viruses demonstrating bio-equivalence. A weekly analysis of the antibody titers to MVA following the different vaccination regimes reveal that vaccinations with MVA-BN significantly enhances the speed and magnitude of the antibody response compared to the other vaccination regimes. Indeed, the antibody titers to MVA are significantly higher ($p>0.05$) at weeks 2, 4 and 5 (1 week post boost at week 4) when vaccinated with MVA-BN which is cultured in serum free medium compared to mice vaccinated with MVA-572 or MVA-575. Following the boost vaccination at week 4, the antibody titers are also significantly higher in the MVA-BN group compared to the mice receiving a single vaccination of either the vaccinia strains Elstree or Wyeth. These results clearly demonstrate that 2 vaccinations with MVA-BN induce a superior antibody response compared to the classical single vaccination with traditional vaccinia strains (Elstree and Wyeth) and confirm the findings that MVA-BN induces a higher specific immunity than other MVA strains.

MVA-Prime and Boost Regimes Generate the Same Level of Protection as DNA-Prime/MVA-Boost Regimes in an Influenza Challenge Model.

The efficacy of MVA prime/boost regimes to generate high avidity CTL responses is assessed and is compared to DNA prime/MVA boost regimes that have been reported to be superior. The different regimes are assessed using a murine polytope construct encoded by either a DNA vector or MVA-BN and the levels of CTL induction were compared by ELISPOT; whereas the avidity of the response is measured as the degree of protection afforded following a challenge with influenza.

Constructs

The DNA plasmid encoding the murine polytope (10 CTL epitopes including influenza, ovalbumin) was described previously (Thomson, et al., 1998, J. Immunol. 160: 1717). This murine polytope is inserted into deletion site II of MVA-BN, which is propagated on CEF cells in serum free medium, sucrose purified and formulated in Tris pH 7.4.

Vaccination Protocols

In the current study, specific pathogen free 6-8 week old female BALB/c (H-2d) mice are used. Groups of 5 mice are used for ELISPOT analysis, whereas 6 mice per group are used for the influenza challenge experiments. Mice are vaccinated with different prime/boost regimes using MVA which is cultured in serum free medium or DNA encoding the murine polytope, as detailed in the results. For immunizations with DNA, mice are given a single injection of 50 μg of endotoxin-free plasmid DNA (in 50 μl of PBS) in the quadricep muscle. Primary immunizations using MVA are done either by intravenous administration of $10^7$ pfu MVA-BN per mouse, or by subcutaneous administration of $10^7$ pfu or $10^8$ pfu MVA-BN per mouse. Boost immunizations are given three weeks post primary immunization. Boosting with plasmid DNA is done in the same way as the primary immunization with DNA (see above). In order to establish CTL responses, standard ELISPOT assays (Schneider et al., 1998, Nat. Med. 4; 397-402) are performed on splenocytes 2 weeks after the last booster immunization using the influenza CTL epitope peptide (TYQ), the *P. Berghei* epitope peptide (SYI), the Cytomegalovirus peptide epitope (YPH) and/or the LCV peptide epitope (RPQ).

For the challenge experiments, mice are infected i.n. with a sub-lethal dose of influenza virus, Mem71 ($4.5\times10^5$ pfu in 50 ml PBS). At day 5 post-infection, the lungs are removed and viral titers are determined in duplicate on Madin-Darby canine kidney cell line using a standard influenza plaque assay.

Efficacy of a MVA-BN nef Vaccine in SIV Infected Rhesus Monkeys To determine the efficacy of a MVA-BN nef vaccine, the viral load and delay of disease following a challenge with a virulent primary isolate of SIV are assessed. Another objective of the study is to determine whether MVA-BN could be used to safely boost immune responses in immune-compromised monkeys with a pre-existing immunity to MVA.

Vaccination Protocols

Two groups (n=6) of rhesus monkeys (*Macaca mulalta*) are vaccinated with a bolus intramuscular injection at week 0, 8 and 16, using either MVA-BN alone which is cultured in serum free medium or a recombinant MVA-BN nef which is cultured in serum free medium. On week 22, all monkeys are challenged with 50 $MID_{50}$ of a pathogenic cell-associated SIV stock (1XC) from primary, uncultured rhesus monkey PBMC by the intravenous route. The clinical status of the animals is frequently monitored and regular blood samples are taken for the measurement of viremia, immune parameters, and a full range of hematology and blood clinical chemistry parameters. Animals that develop AIDs-like disease are sacrificed. The surviving monkeys are monitored for 99 weeks post vaccination. At week 100 the surviving monkeys are immunized i.m. with MVA-BN tat which is cultured in serum free medium and receive further immunizations with the same MVA-BN tat week 102 and 106.

This study demonstrates that MVA-BN which is cultured in serum free media is able to prime/boost immune responses in immune-compromised rhesus monkeys. It also demonstrates that MVA-BN immunizations are safe and do not affect the levels of viremia in SIV infected animals. The delay in the progression of AIDS-like disease in the animals vaccinated with the MVA-BN nef, which is cultured in serum free medium, indicates that an immune response is successfully generated to nef.

Therapeutic Vaccination of SIV-Infected Monkeys Undergoing Anti-Retroviral Treatment An MVA-BN based therapeutic HIV vaccine is likely to be used in individuals undergoing anti-retroviral therapy. Therefore, this study is designed to investigate the safety (effect on SIV levels) and efficacy of recombinant MVAs encoding a variety of SIV antigens (gag, pol, env, rev, tat, and nef) in SIV infected monkeys treated with PMPA. PMPA is a nucleoside analogue that is effective against HIV and SIV (Rosenwirth, B. et al., 2000, J Virol 74, 1704-11).

Constructs

All the recombinant MVA constructs are propagated on CEF cells in serum free media, sucrose purified and formulated in Tris pH 7.4.

Vaccination Protocol

Three groups (n=6) of rhesus monkeys (*Macaca mulatta*) are infected with 50 $MID_{50}$ of a pathogenic primary Sly isolated (1XC) and then treated daily with PMPA (60 mg/kg given s.c.) for 19 weeks. At week 10, animals are vaccinated with recombinant MVA-BN (i.m.), or saline, and receive identical vaccinations 6 weeks later. Group 1 receives a mixture of MVA gag-pol and MVA-env, group 2 receives MVA-tat, MVA-rev and MVA-nef, whereas Group 3 receives saline. The clinical status of the animals is frequently monitored and regular blood samples are taken for the measurement of viremia, immune parameters, and a full range of hematology and blood clinical chemistry parameters.

* * *

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

We claim:

1. A method for the re-derivation of a modified vaccinia Ankara virus comprising:
   a) infecting chicken embryo fibroblast cells, which have not previously been cultured in a medium containing serum, with a modified vaccinia Ankara virus;
   b) cultivating the infected cells in a serum free medium comprising epidermal growth factor at a concentration of 1-50 ng/ml; and
   c) isolating the virus produced by the infected cells.

2. The method of claim 1, wherein the serum free medium comprises a fibronectin.

3. The method of claim 1, wherein the epidermal growth factor is human epidermal growth factor.

4. The method of claim 3, wherein the epidermal growth factor is recombinant human epidermal growth factor at a concentration of 5-50 ng/ml.

5. The method of claim 4, wherein the epidermal growth factor is recombinant human epidermal growth factor at a concentration of 5-20 ng/ml.

6. The method of claim 5, wherein the serum free medium comprises human plasma fibronectin at a concentration of 1-10 $\mu g/cm^2$.

7. The method of claim 5, wherein the serum free medium comprises a microbial extract, a plant extract, or an extract from a non-mammalian animal.

8. The method of claim 5, wherein the serum free medium comprises asparagine in the range of 0.8-1.8 mM.

9. The method of claim 5, wherein the serum free medium comprises glutamine in the range of 1-5 mM.

10. The method of claim 1, wherein the infected cells are cultivated as adherent cells attached to a solid support.

11. The method of claim 5, wherein the infected cells are cultivated as adherent cells attached to a solid support.

12. The method of claim 1, wherein the infected cells are cultivated in suspension culture.

13. The method of claim 5, wherein the infected cells are cultivated in suspension culture.

14. The method of claim 1, wherein the modified vaccinia Ankara virus is passaged only one time in the serum free medium.

15. The method of claim 5, wherein the modified vaccinia Ankara virus is passaged only one time in the serum free medium.

16. The method of claim 1, wherein the modified vaccinia Ankara virus is passaged 1-8 times in the serum free medium.

17. The method of claim 1, wherein the modified vaccinia Ankara virus is passaged 3-8 times in the serum free medium.

18. The method of claim 5, wherein the modified vaccinia Ankara virus is passaged 3-8 times in the serum free medium.

19. The method of claim 1, wherein the modified vaccinia Ankara virus is passaged 4-6 times in the serum free medium.

20. The method of claim 5, wherein the modified vaccinia Ankara virus is passaged 4-6 times in the serum free medium.

* * * * *